(12) United States Patent
Watkins et al.

(10) Patent No.: US 11,554,372 B1
(45) Date of Patent: Jan. 17, 2023

(54) BINDING ASSAY WITH NO WASH STEPS OR MOVING PARTS USING MAGNETIC BEADS

(71) Applicant: Fitbit LLC, San Francisco, CA (US)

(72) Inventors: Herschel Watkins, Woodacre, CA (US); Kristy McKeating, San Francisco, CA (US)

(73) Assignee: FITBIT LLC, San Francsco, CA (US)

( * ) Notice: Subject to any disclaimer, the term of this patent is extended or adjusted under 35 U.S.C. 154(b) by 0 days.

(21) Appl. No.: 17/546,565

(22) Filed: Dec. 9, 2021

Related U.S. Application Data

(63) Continuation of application No. PCT/US2021/041988, filed on Jul. 16, 2021.

(51) Int. Cl.
*B01L 3/00* (2006.01)
*G01N 33/543* (2006.01)

(52) U.S. Cl.
CPC ..... *B01L 3/50273* (2013.01); *B01L 3/502707* (2013.01); *B01L 3/502715* (2013.01);
(Continued)

(58) Field of Classification Search
CPC .......... B01L 3/50273; B01L 3/502715; B01L 3/502753; B01L 3/502707; B01L 2200/04;
(Continued)

(56) References Cited

U.S. PATENT DOCUMENTS 4,868,131 A 9/1989 Hiratsuka
10,293,340 B2 * 5/2019 Mai ................... B01L 3/502715
(Continued)

FOREIGN PATENT DOCUMENTS

JP 2014149172 A 8/2014
WO WO 2018/097796 5/2018
WO WO 2019/074760 4/2019

OTHER PUBLICATIONS

Clotilde et al., "Multiplex Immunoassay: a Planar Array on a Chip Using the MagArray™ Technology", ELISA: Methods and Protocols, Methods in Molecular Biology, vol. 1318, pp. 119-126.
(Continued)

*Primary Examiner* — Brian J. Sines
(74) *Attorney, Agent, or Firm* — Dority & Manning, P.A.

(57) ABSTRACT

This present disclosure provides devices, systems, and methods for performing point-of-care analysis of a target analyte in a biological fluid via a binding assay. The present disclosure includes a cartridge for collecting the target analyte contained in a fluid sample and performing an assay. The cartridge includes an assay stack having a first separation layer, a second separation layer, and a detection membrane. The cartridge also includes a plurality of first complexes comprising a capture molecule and a magnetic bead and a plurality of second complexes comprising a detection molecule and a detection label. Further, the detection membrane includes a substrate that interacts with the detection label to elicit a quantifiable response in the presence of the target analyte. The quantifiable response corresponds to an amount of detection antibody present in the detection membrane, and the amount of detection antibody present corresponds to an amount of the target analyte present.

13 Claims, 17 Drawing Sheets

(52) U.S. Cl.
CPC ..... *B01L 3/502753* (2013.01); *B01L 2200/04* (2013.01); *B01L 2200/0605* (2013.01); *B01L 2200/0689* (2013.01); *B01L 2200/12* (2013.01); *B01L 2200/16* (2013.01); *B01L 2300/0663* (2013.01); *B01L 2300/0681* (2013.01); *B01L 2300/0864* (2013.01); *B01L 2300/0887* (2013.01); *B01L 2300/126* (2013.01); *B01L 2400/043* (2013.01); *G01N 33/54326* (2013.01); *G01N 33/54346* (2013.01)

(58) Field of Classification Search
CPC ...... B01L 2200/0605; G01N 33/54326; G01N 33/54346
See application file for complete search history.

(56) References Cited

U.S. PATENT DOCUMENTS

| | | | |
|---|---|---|---|
| 2007/0178521 A1* | 8/2007 | Sakaino | B01L 3/502753 435/7.1 |
| 2010/0311186 A1 | 12/2010 | Gregory et al. | |
| 2015/0241423 A1 | 8/2015 | Dilleen et al. | |
| 2021/0055289 A1 | 2/2021 | Johannsen et al. | |

OTHER PUBLICATIONS

Dutta et al., "Wash-free, label-free immunoassay for rapid electrochemical detection of PfHRP2 in whole blood samples", Scientific Reports, www.nature.com/scientificreports, Nov. 20, 2018, 8 pages.

Afriat et al., "Development of a point-of-care technology for bacterial identification in milk", Taianta, vol. 219, Nov. 1, 2020, 8 pages.

Eltzov et al., "Colorimetric stack pad immunoassay for bacterial identification", Biosensors and Bioelectronics, vol. 87, Jan. 15, 2017, pp. 572-578.

Eltzov et al., "Miniaturized Flow Stacked Immunoassay for Detecting *Escherichia coli* in a Single Step", Anal. Chem., 2016, 88, 12, pp. 6441-6449.

Harpaz et al., "Enhanced Colorimetric Signal for Accurate Signal Detection in Paper-Based Biosensors", Diagnostics 2020, 10, 28, 15 pages.

Harpaz et al., "Point-of-Care-Testing in Acute Stroke Management: an Unmet Need Ripe for Technological Harvest", Biosensors 2017, 7, 30, 39 pages.

International Search Report and Written Opinion for Application No. PCT/US2021/041988, dated Apr. 12, 2022, 17 pages.

* cited by examiner

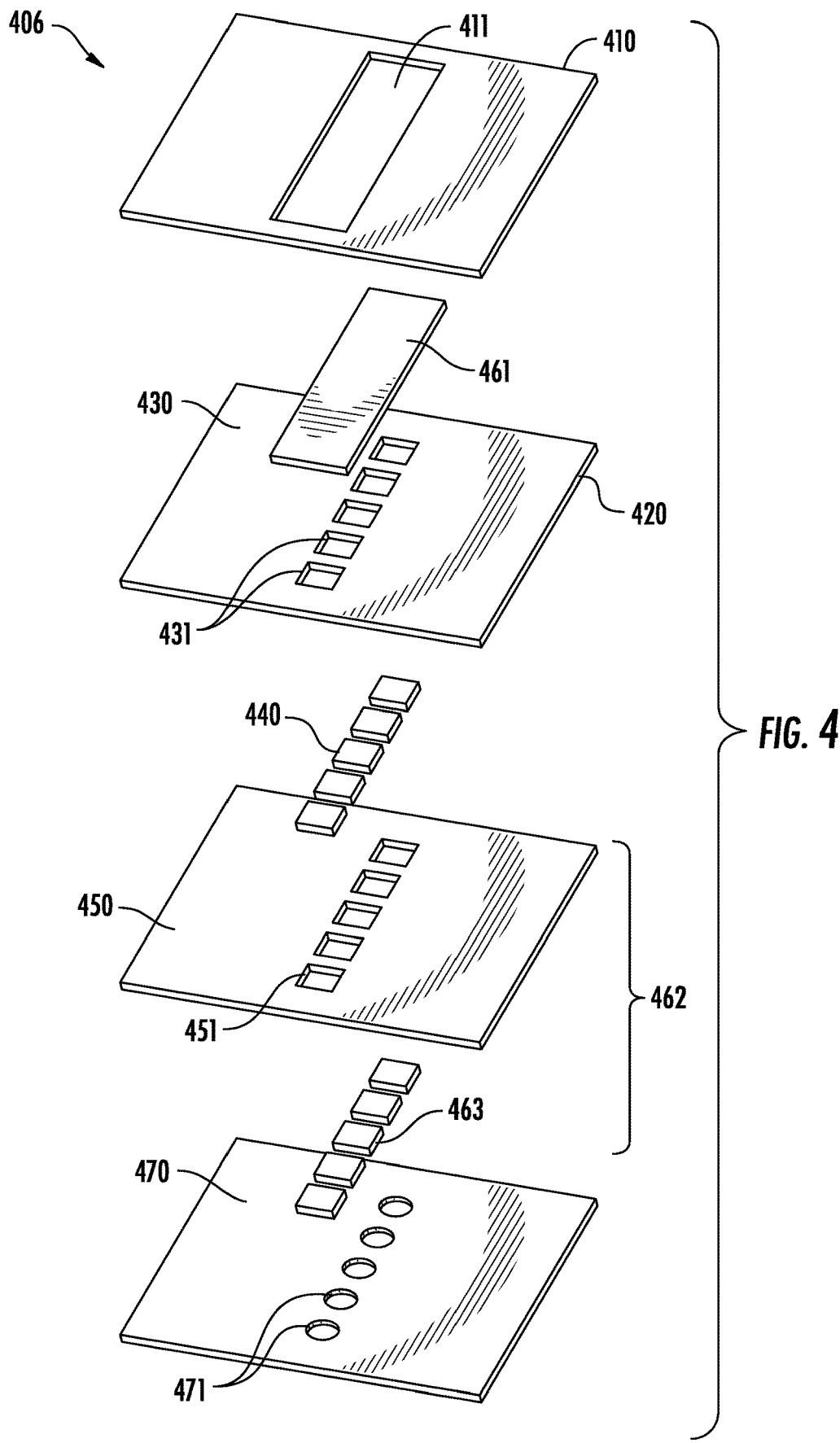

BINDING ASSAY WITH NO WASH STEPS OR MOVING PARTS USING MAGNETIC BEADS

PRIORITY CLAIM

The present application is a continuation of PCT International Patent Application No. PCT/US2021/041988 having a filing date of Jul. 16, 2021. Applicant claims priority to and the benefit of said application and incorporates said application herein by reference in its entirety.

FIELD

The present disclosure relates generally to a point-of-care (POC) testing system. More particularly, the present disclosure relates to systems and methods for performing a binding assay without any wash steps, incubation steps, or moving parts.

BACKGROUND

Point-of-care (POC) testing refers to performing medical diagnostic tests at the time and place that the patient is being treated. POC testing is advantageous over traditional diagnostic testing where patient samples are sent out to a laboratory for further analysis, because the results of traditional diagnostic tests may not be available for hours, if not days or weeks, making it difficult for a caregiver to assess the proper course of treatment in the interim.

Typically, when measuring certain chemical analytes in biological fluids such as blood, binding assays such as immunoassays are the gold standard for detecting such chemical analytes. However, binding assays are rarely, if ever, used in POC diagnostics because they conventionally require several wash steps and several incubation steps. This makes the binding assays difficult to incorporate into POC testing systems due to the complexity in conducting the binding assays properly and accurately in a POC environment.

For instance, designing POC testing systems for in-home use is particularly challenging, because such systems are often operated by people with limited training or no training at all. Current systems can often require the user to follow multiple steps of operations of multiple separated parts, where user-introduced errors can easily cause inaccurate or failed assays.

Further, in most POC testing systems for blood samples, certain sample preparation steps need to be performed prior to a final chemical reaction that provides the test result. These sample preparation steps may include complex preparation steps such as plasma separation, cell lysis, incubation, wash steps, or others, depending on the assay. The time required to complete such complex preparation steps may be comparable to the time required for blood to undergo undesirable clotting, which further introduces error into the assay results. While many attempts to solve this problem have been proposed or implemented, these solutions often employ complex fluidics or moving parts to create the necessary incubation times and wash steps, and such mechanisms result in increases in cost, failure rate, and complexity.

Thus, it would be desirable to have a POC system that can detect a target analyte using a binding assay that addresses the aforementioned problems.

SUMMARY

Aspects and advantages of embodiments of the present disclosure will be set forth in part in the following description, or can be learned from the description, or can be learned through practice of the embodiments.

One example aspect of the present disclosure is directed to a cartridge for collecting a target analyte contained in a biological fluid sample and performing an assay on the target analyte. The cartridge includes an assay stack having a first separation layer. The assay stack also includes a plurality of first complexes having a capture molecule and a magnetic bead; a plurality of second complexes having a detection molecule and a detection label; a second separation layer; and a detection membrane. The detection membrane includes a substrate that interacts with the detection label to elicit a quantifiable response in the presence of the target analyte. The quantifiable response corresponds to an amount of detection molecule present in the detection membrane, and the amount of detection molecule present in the detection membrane corresponds to an amount of the target analyte present in the fluid sample.

Another aspect of the present disclosure is directed to a method of fabricating a cartridge. The method includes, in no particular order, the steps of: applying a plurality of first complexes comprising a capture molecule and a magnetic bead and a plurality of second complexes comprising a detection molecule and a detection label to a first separation layer; allowing the plurality of first complexes and the plurality of second complexes to dry on the first separation layer; applying a substrate to a detection membrane; allowing the substrate to dry on the detection membrane; and positioning a second separation layer between the first separation layer and the detection membrane. Further, the substrate is configured to interact with the detection label to elicit a quantifiable response in the presence of a target analyte in a fluid sample that is introduced to the cartridge, the quantifiable response corresponds to an amount of detection molecule present in the detection membrane, and the amount of detection molecule present in the detection membrane corresponds to an amount of the target analyte present in the fluid sample.

Still another aspect of the present disclosure is directed to a system for collecting a target analyte contained in a fluid sample and performing an assay on the target analyte. The system includes an assay stack, wherein the assay stack comprises a first separation layer; a plurality of first complexes comprising a capture molecule and a magnetic bead; a plurality of second complexes comprising a detection molecule and a detection label; a second separation layer; and a detection membrane, wherein the detection membrane includes a substrate that interacts with the detection label to elicit a quantifiable response in the presence of the target analyte, wherein the quantifiable response corresponds to an amount of detection molecule present in the detection membrane, and wherein the amount of detection molecule present in the detection membrane corresponds to an amount of the target analyte present in the fluid sample; and an electromagnet for pulling a third complex comprising the target analyte bound to one of the first complexes and one of the second complexes through the second separation layer to the detection membrane.

Still another aspect of the present disclosure is directed to an in-vitro use of the proposed cartridge for performing an assay on a target analyte in an isolated fluid sample.

Yet another aspect of the present disclosure is directed to a use of a cartridge in a diagnostic method for performing an assay on a target analyte in an isolated fluid sample.

These and other features, aspects, and advantages of various embodiments of the present disclosure will become better understood with reference to the following description and appended claims. The accompanying drawings, which are incorporated in and constitute a part of this specification, illustrate example embodiments of the present disclosure and, together with the description, serve to explain the related principles.

BRIEF DESCRIPTION OF THE DRAWINGS

Detailed discussion of embodiments directed to one of ordinary skill in the art is set forth in the specification, which makes reference to the appended figures, in which:

FIG. 4 illustrates various layers of an assay stack contained within the cartridge;

Figure 1:
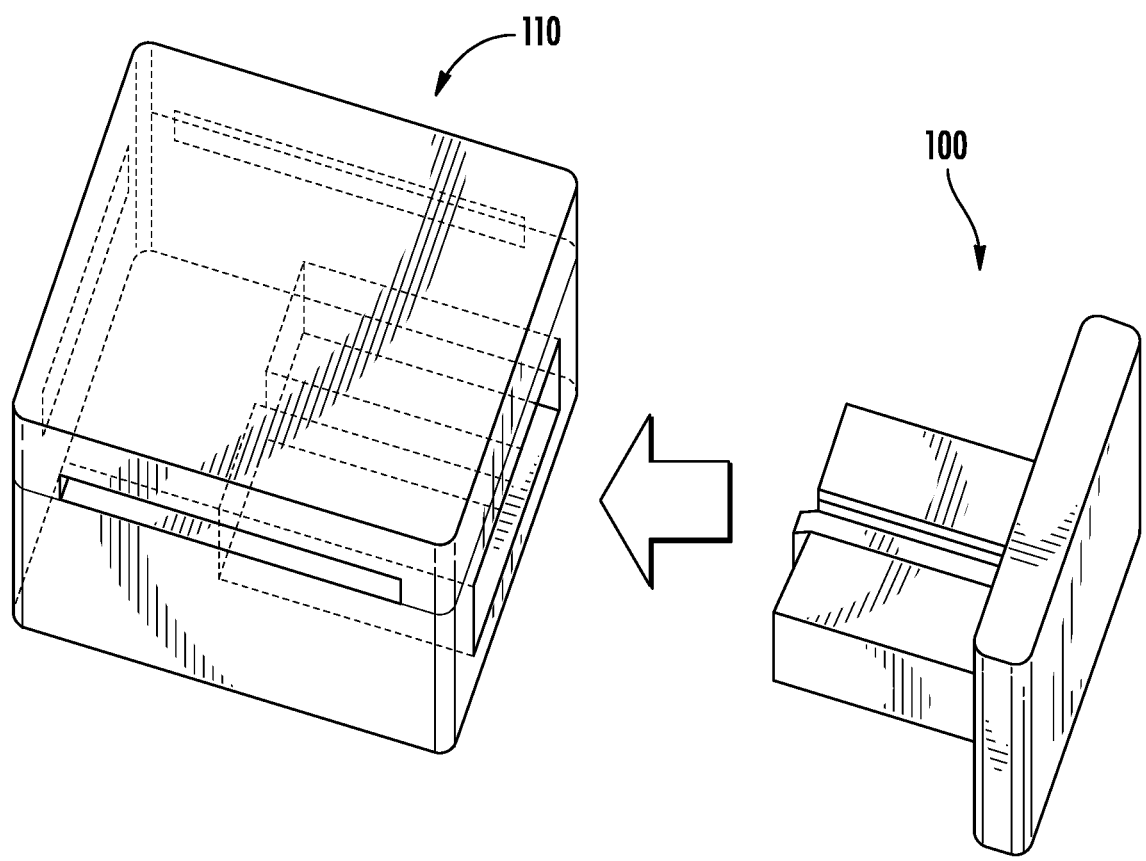
FIG. 1 provides a schematic drawing of a system comprising a cartridge and an assay reader according to one embodiment of the disclosure.

Reference numerals that are repeated across plural figures are intended to identify the same features in various implementations.

DETAILED DESCRIPTION

Any of the features, components, or details of any of the arrangements or embodiments disclosed in this application, including without limitation any of the cartridge embodiments and any of the testing or assay embodiments disclosed below, are interchangeably combinable with any other features, components, or details of any of the arrangements or embodiments disclosed herein to form new arrangements and embodiments.

Generally, the present disclosure is directed to a device and a system for rapid POC detection of a target analyte contained in a biological fluid sample and the subsequent analysis of the target analyte via an immunoassay or other binding type assay that does not require any wash steps and that does not require any moving parts. The binding assay may also be performed without any incubation steps in some embodiments. The present disclosure also provides methods and systems for using the device to analyze the fluid sample via an immunoassay or other binding type assay to quantify the level of the target analyte that is present in the fluid sample.

The device can be in the form of a cartridge that includes an assay stack. The assay stack includes a first separation layer, a second separation layer, and a detection membrane containing a substrate that interacts with the detection label to elicit a quantifiable response. The second separation layer can be arranged between the first separation layer and the detection membrane. A plurality of first complexes that each include a capture molecule and a magnetic bead and a plurality of second complexes that each include a detection molecule and a detection label can be dried onto the first separation layer, where it is to be understood that the capture molecule and the detection molecule are chosen based on their ability to bind with the target analyte. Upon contact of a fluid sample with the first separation layer, any target analyte present in the fluid sample will couple with the first complexes and the second complexes to form one or more third complexes. In an exemplary embodiment, an electromagnet can be activated to pull any third complexes through the second separation layer to the detection membrane, while any unbound second complexes remain in the second separation layer. It is also to be understood that any unbound first complexes will also be pulled through the second separation layer to the detection membrane. However, because such unbound first complexes will not be coupled to a target analyte, detection molecule, or detection label, the presence of the unbound first complexes in the detection membrane will not affect the accuracy of the binding assay. Thereafter, the substrate can interact with the detection label to elicit a quantifiable response (e.g., colorimetric, fluorescent, electrochemical, etc.) in the presence of the target analyte. The quantifiable response can correspond to an amount of detection molecule present in the detection membrane, and the amount of detection molecule present in the detection membrane can correspond to an amount of the target analyte present in the fluid sample. It is to be understood that any binding assay known to one of ordinary skill in the art can be utilized in the systems and devices of the present disclosure, such as, but not limited to sandwich assays, competition assays, or labeled-antigen assays. Further, although immunoassays are described in the embodiments below, other detection and capture molecules in addition to antibodies are also contemplated by the present disclosure.

The proposed solution allows for providing a compact POC testing system capable of an in-vitro assay of an isolated (biological) fluid sample without wash and incubation steps and thus without the need for physical washing or complex moving parts in the POC system. A cartridge constructed as proposed with an assay stack comprising a second separation layer sandwiched between a first separation layer and a detection membrane in this context allows for a cost-efficient and—compared to conventional POC testing systems—less complex detection of a target analyte in a fluid sample. In combination with a proposed assay reader, the detection may be automated in an easy way, since any target analyte present in the fluid sample may join to the plurality of first complexes and the plurality of second complexes to create a third complex and the third complex can then be pulled through the assay stack at a specified point in time upon activation of an electromagnet of the assay reader. Based on the detection membrane allowing for qualitatively or even quantitatively determining the amount of target analyte in the sample fluid based on a resulting signal (e.g., a color change), also an automated assessment on the presence of target analyte in the fluid sample is possible.

Further, it should be understood that when the electromagnet is not activated, the first and second complexes have time to interact with the target analyte in the fluid sample before moving through the assay stack to the detection membrane once the electromagnet is activated to pull any third complexes through to the detection membrane. This allows for precise control of the fluid sample incubation time, where such precise control is not possible in many other assay platforms, much less with a physical washing step.

With reference now to the figures, example embodiments of the present disclosure will be discussed in further detail. First, the components of the cartridge and assay reader will be discussed, followed by the components used to perform an immunoassay as contemplated by the present disclosure.

FIG. 1 shows a POC testing system according to one exemplary embodiment of the present disclosure. The POC testing system comprises a cartridge 100 and an assay reader 110. As described herein, cartridge 100 is used to collect the biological sample that may potentially contain a target analyte. The collection process also distributes the target analyte within cartridge 100. After the target analyte is collected in cartridge 100, the user inserts cartridge 100 into assay reader 110. As described herein, the act of inserting cartridge 100 into assay reader 110 results in the compression of cartridge 100, thereby causing the target analyte to be distributed to a plurality of assay pads. In this way, the act of inserting cartridge 100 into assay reader 110 commences one or more assay reactions that provide information regarding the contents of the target analyte. However, it is also to be understood that other insertion approaches are contemplated that do not require compression. Further, it is to be understood that while multiple assays can be utilized to determine the contents of a target sample, each assay is generally specific for one particular target analyte. As described herein, assay reader 110 is equipped with a detection system that is used to detect the results of the one or more assay reactions that occur at one or more assay pads of cartridge 100. The detection system is not particularly limited and may be a detection system which causes a measurable signal change as the result of an assay reaction. Non-limiting examples of suitable detection systems include colorimetric, fluorescence, electrochemical, and optical detection systems as described herein and any other detection system that would be understood by one of ordinary skill in the art.

Figure 2A:
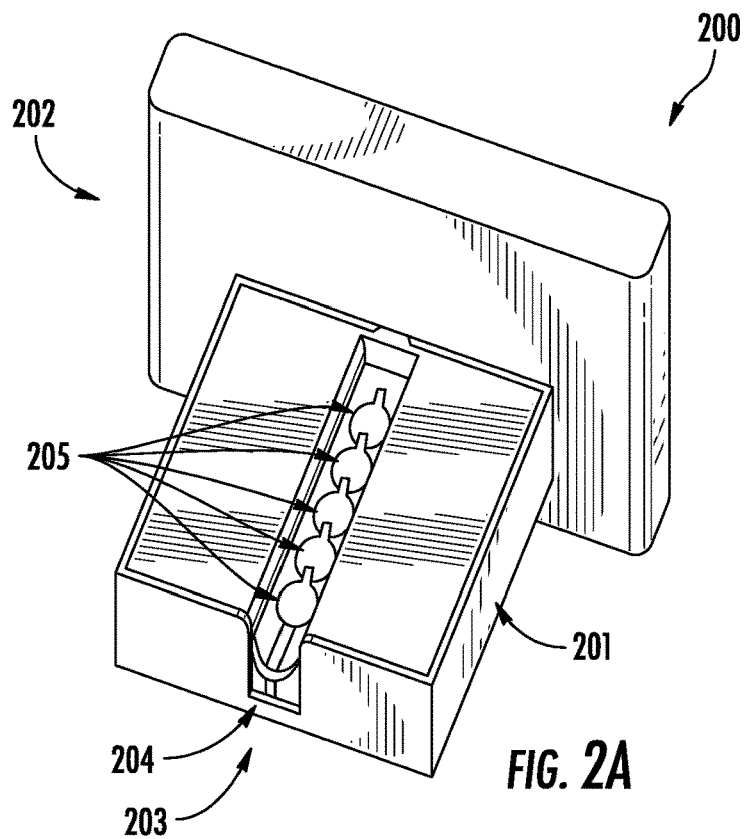
FIGS. 2A-2C illustrate an embodiment of the cartridge utilized in the system.
Figure 2B:
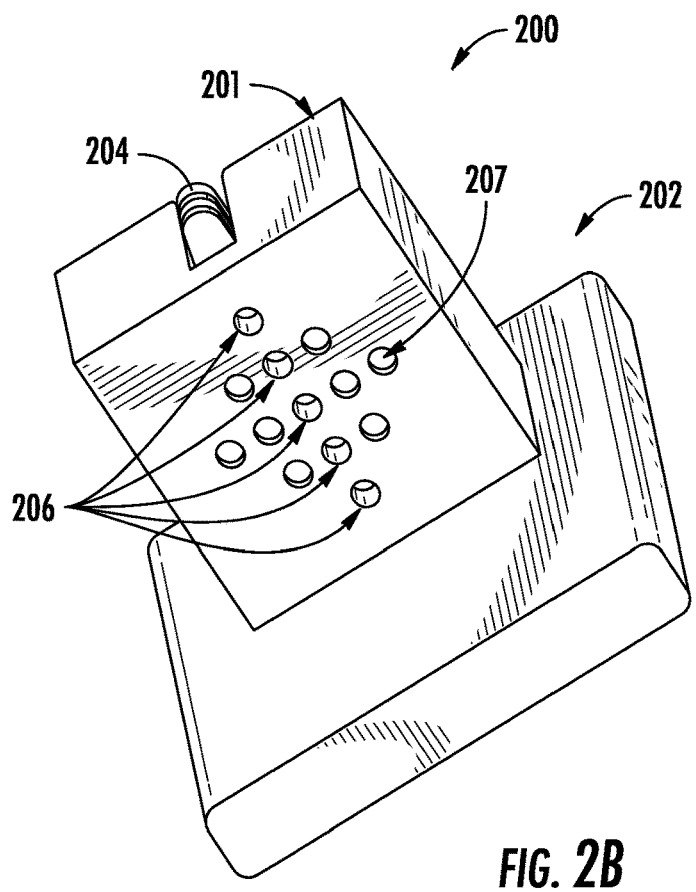

FIG. 2A illustrates a top, perspective view of an embodiment of cartridge 100 in the form of a cartridge 200. In FIG. 2A, cartridge 200 includes a housing 201 attached to a handle 202. In general, cartridge 200 is designed to be easy to handle by the user and to provide a protective shell for the microfluidic distribution system and assay components housed within cartridge 200. In general, suitable materials for housing 201 and handle 202 include polyolefinic compounds, such as polyethylene, polypropylene, and other polymeric resins or compounds known in the medical device manufacturing art. During sample collection, cartridge 200 is brought into contact with a target analyte in a fluid sample (e.g., blood). The target analyte is drawn into channel 203 and via channel opening 204 by capillary action. In some embodiments, channel 203 comprises a plurality of receiving chambers 205 located along channel 203. In some embodiments, each receiving chamber is positioned between two venting holes, which facilitate the division of the target analyte in the channel into multiple aliquots which flow to the assay pads in the assay stack. It should be recognized that the channel opening 204 can function as a venting hole and that neighboring receiving chambers can share a common venting hole between them. The venting holes, in combination with the porous or mesh material described herein, prevent unwanted bubble formation as the target analyte is drawn into the receiving chambers. FIG. 2B illustrates a bottom view of an embodiment of the cartridge 200. In FIG. 2B, the bottom portion of housing 201 comprises a plurality of assay detection ports 206 aligned with channel opening 204. The assay detection ports 206 permit the assay results to be interrogated, for example, by optical detection methods as described herein. In addition, the bottom portion of housing 201 may comprise plurality of holes 207, which are additional assay detection ports that may be used with assay components and microfluidic channels that are arranged in a corresponding configuration.

Figure 2C:
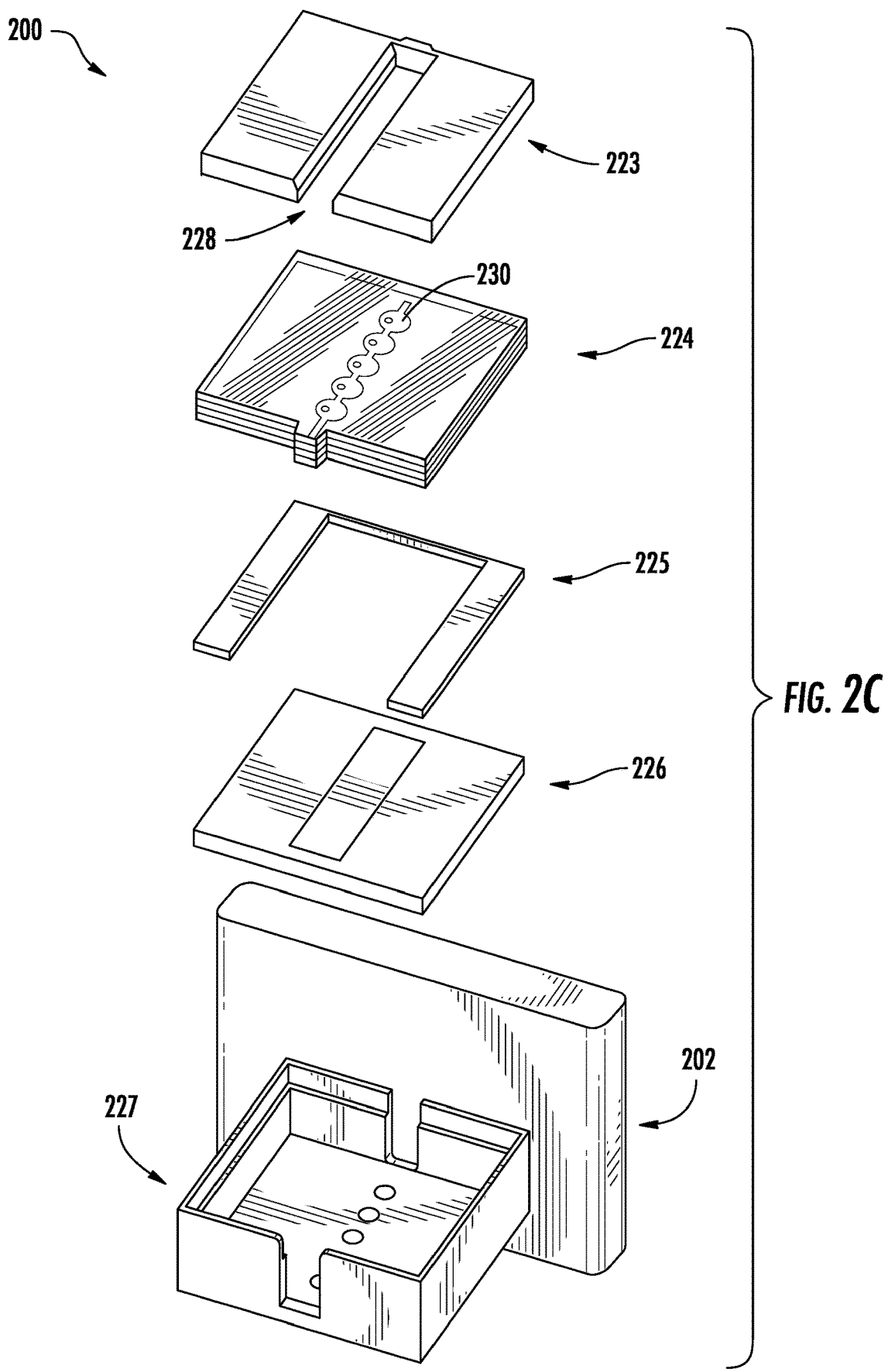

FIG. 2C provides an exploded view of the components of the cartridge 200, according to one embodiment of the present disclosure. In FIG. 2C, the outer shell of cartridge 200 includes the handle 202, bottom housing portion 227, and a cap 223 that is equipped with a slot 228. The bottom housing portion 227 can be a cuboid shape enclosure with one open side. The enclosure shape of the bottom housing portion 227 protects the components within the interior chamber and can avoid accidental actuation of the system. The cap 223 can fit to the open side of the bottom housing portion 227 and have a shape and size that corresponds to the open side of the bottom housing portion 227. When the bottom housing portion 227 and cap 223 of the housing are assembled together, an interior chamber can be formed for enclosing other components of the cartridge within the interior chamber. In other embodiments, the cap 223 and bottom housing portion 227 do not form an enclosure with an interior chamber and can be rigid structures positioned on the top of a metering stack and bottom of an assay stack, which are described herein.

In preferred embodiments, bottom housing portion 227 and cap 223 can be formed of a material to provide a rigid structure to the cartridge 200. For example, the bottom housing portion 227 and the cap 223 can be a plastic material, as described herein. The bottom housing portion 227 and cap 223 can be moveable or non-moveable with relation to each other. In some embodiments, when cartridge 200 is inserted into an assay reader, the components within the interior chamber are compressed to cause at least one portion of the collected target analyte to be delivered to a plurality of assay components. The compression can be caused by the user closing a lid of the assay reader, for example. However, it is also to be understood that other approaches for insertion of the cartridge 200 into an assay reader are contemplated that do not require compression.

In some embodiments, the cartridge does not include a cap and bottom housing portion. In such embodiments, the cartridge does not include the housing 201 (see e.g., FIG. 2A) and the metering stack and assay stack can be inserted into an assay reader without an enclosure around it.

As shown in FIG. 2C, cartridge 200 can include a metering stack 224, a spacer material 225, and an assay stack 226. The metering stack 224 can be used to collect a sample of a biological fluid (e.g., blood) and the assay stack 226 comprises assay components necessary for a binding assay (e.g., an immunoassay) to be carried out as discussed in detail herein. As used herein, the term "metering" refers to collecting a liquid sample of a biological fluid and delivering one or more predetermined volumes of at least a portion of the fluid to the assay components for further analysis via the assay components contained in the assay stack. When assembled into a cartridge, the metering stack 224, a spacer material 225, and an assay stack 226 can be arranged in a stack.

The spacer material 225 is a compressible layer that may be positioned between the metering stack 224 and assay stack 226 as shown in FIG. 2C. In an embodiment, the spacer material 225 may be a flexible material that can be compressed in the vertical direction when the cartridge is inserted into the assay reader and the metering stack 224 is moved into contact with or close proximity to the assay stack 226. In some embodiments, the spacer material 225 can be a flexible material, such as foam, rubber, porous polymer, metal, cotton, or other bending, folding, or moving mechanisms such as a clamp or spring. In some embodiments, the metering and assay stacks are initially separated by an air gap maintained by the spacer material 225. In certain embodiments, spacer material 225 is physically affixed to another layer, such as metering stack 224 or assay stack 226 before the layers of the cartridge are brought together. Typically, the metering and assay stacks remain separated throughout the sample collection process. In such embodiments, the separation between the metering stack and the assay stack can prevent a chemical reaction from starting during the target analyte collection step. When the spacer material 225 is compressed, the metering stack 224 and assay stack 226 can come into contact with or brought into close proximity to each other.

In preferred embodiments, when the metering stack is fully filled with a biological fluid, the cartridge is inserted into an assay reader. Preferably, the material that is used for the top surface of channel 230 is sufficiently transparent so that a user can determine by visual inspection when the channel 230 is filled and the cartridge is ready for insertion into the assay reader. The assay reader is configured to accept the cartridge and comprises a mechanism that compresses the spacer material, thereby pushing the metering stack and assay stack together when the cartridge is inserted into the assay reader. The compression of the spacer material causes a predetermined volume of at least a portion of the collected fluid to flow to assay components in the assay stack. In this way, the act of compressing the metering stack and assay stack together can, in certain embodiments, provide a well-defined point in time that marks the start of the immunoassay or other binding type assay through the components in the assay stack. However, it is also to be understood that other insertion approaches are contemplated that do not require compression of the metering stack and assay stack together as would be understood by one of ordinary skill in the art.

In some embodiments, the biological fluid containing the target analyte is blood, and the cartridge can be used to collect a sample of blood from a skin prick and deliver the sample to the assay stack consistently with minimal user intervention. The user, with a regular pricking lancet, can elicit bleeding in a suitable body site such as a fingertip, palm, hand, forearm, stomach area, etc. Once a drop of blood of sufficient volume is on the skin, the user can collect it by touching the tip of the cartridge to the blood drop. Once the metering stack is fully filled with blood, the user can insert the cartridge into the assay reader, which triggers the delivery of the blood sample to the assay stack. In some embodiments, this can be performed by a patient, administrator, or healthcare provider. The blood collection and testing as described herein does not have to be performed by a trained health care professional.

In addition, the cartridge design can allow for dispensing different pre-defined volumes of blood sample to multiple assay locations, without using any moving parts such as pumps or valves in the cartridge or in the assay reader. This increases the accuracy and flexibility of a multiplexed quantitative POC analysis, while reducing the complexity and cost of the cartridge and the assay reader.

Typically, as illustrated in FIG. 2C, the metering stack 224 includes a channel 230 to contain the target analyte (e.g., an analyte of interest contained in a blood sample). In certain embodiments, the channel 230 can hold a volume of biological fluid containing a target analyte in the range of about 0.5 to about 100 µl, about 5 µl to about 90 µl, about 10 to about 80 µl, about 20 µl to about 60 µl, or about 30 µl to about 50 µl. The volume of the target analyte can be controlled by the dimensions of the channel, including the shape, width, length, and depth of the channel, as described herein. In some embodiments, the depth of the channel can be in the range of about 5 µm to about 3 mm, about 10 µm to about 2 mm, or about 250 µm to about 1 mm. In some embodiments, the width of the channel can be in the range of about 100 µm to about 10 mm, about 250 µm to about 5 mm, about 500 µm to about 3 mm, or about 750 µm to about 1 mm. In certain preferred embodiments, the dimensions of the channel are selected such that the target analyte is drawn into the channel by capillary action.

Figure 3:
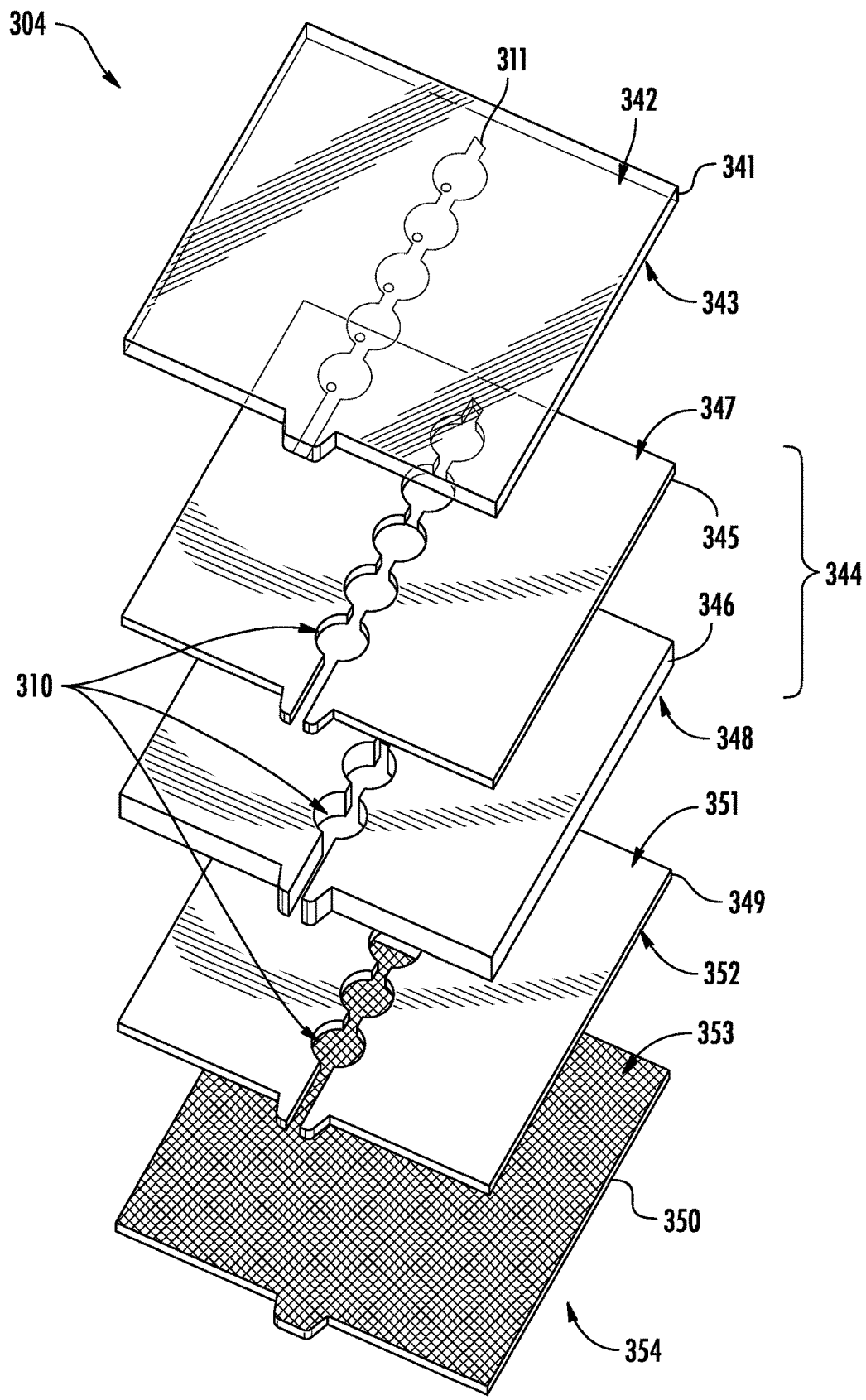
FIG. 3 illustrates various layers of a metering stack contained within the cartridge.

Preferably, the metering stack 224 is designed to direct the target analyte fluid to flow into the channel 230 and into any receiving chamber(s) that may be present. In some embodiments, the channel 230 can be formed of or coated with a hydrophilic material, non-limiting examples of which include 93210 hydrophilic PET (Adhesives Research, Glen Rock Pa.) or 9984 Diagnostic Microfluidic Surfactant Free Fluid Transport Film, 9960 Diagnostic Microfluidic Hydrophilic Film, or 9962 Diagnostic Microfluidic Hydrophilic Film (3M Oakdale, Minn.). The channel 230 can also have one or more porous or mesh material(s) along at least some portions of the channel 230 that allows at least a portion of the biological fluid containing the target analyte to be dispensed from the channel 230 of the metering stack 224 to contact assay components in the assay stack. In one non-limiting embodiment, the metering stack layer includes a porous or mesh material that can be positioned such that the porous or mesh material is aligned with the channel portion on the metering stack's top surface and the assay distribution ports and assay components on the metering stack's bottom surface. In some embodiments, the porous or mesh material is selected such that the pores in such material separate the target analyte into a portion that is to be delivered to the assay components and a portion that is not delivered to the assay components. For example, when the biological fluid containing the target analyte is blood, the pores of the porous or mesh material may be of a size that is suitable for separating erythrocytes from other blood components, such as plasma. In this way, when the cartridge is inserted into the assay reader to perform the assays, only plasma is delivered to the assay components for analysis. Of course, combinations of porous or mesh materials may be used such that the entire biological fluid is delivered to some of the assay components, while only portions of the biological fluid may be delivered to other assay components. For example, the combination of porous or mesh materials may allow only plasma to reach some assay components but allow for the delivery of all blood components to other assay components. In certain embodiments, the channel can include a porous or mesh material at the bottom of the channel. The porous or mesh material at the bottom of the channel can be a hydrophilic material or a material coated with a hydrophilic coating or treatment. In some embodiments, the porous or mesh material can have a pore size between about 1 µm to about 500 µm. Advantageously, when the biological fluid containing the target analyte is blood, the pores of the porous or mesh material can be sized to allow the porous or mesh material to hold the blood sample in the channel without dripping during blood collection and to be absorbed by the assay stack during the blood dispensing step which occurs upon insertion of the cartridge into the assay reader. In some embodiments, the porous or mesh material can also be used to release air and prevent bubble formation during the time that channel is filled with the biological fluid FIG. 3 illustrates an exploded view of a metering stack 304 according to one exemplary embodiment of the present disclosure, where such metering stack 304 can be used as metering stack 224 in the embodiment of FIGS. 2A to 2C. In FIG. 3, the metering stack 304 is formed by assembling multiple layers. The first layer 341 can be a plastic sheet with a first side 342, which is in communication with the surrounding environment when the cartridge is located outside the assay reader, and a second side 343 that faces the assay stack. In some embodiments, the first layer 341 may be a cover layer or top layer of the metering stack. In preferred embodiments, first layer 341 may have a hydrophilic surface or coating on second side 343. Non-limiting examples of suitable hydrophilic surfaces coatings include polyvinylpyrrolidone-polyurethane interpolymer, poly(meth)acrylamide, maleic anhydride polymers, cellulosic polymers, polyethylene oxide polymers, and water-soluble nylons or derivatives thereof, to name just a few. The presence of the hydrophilic surface or coating on second side 343 helps to draw the target analyte into the channel, since most, if not all, of the target analytes are aqueous mixtures, such as blood. The first layer 341 may include venting holes 311 positioned to align with the channel 310 defined by the layers below. In FIG. 3, for example, the venting holes 311 are aligned with the receiving chambers of channel 310 to allow air that otherwise would be trapped as an air bubble in the receiving chamber during channel filling to escape efficiently into the surrounding environment. It should be noted that the channel opening can also serve as a vent hole, if desired. In certain preferred embodiments, the first layer 341 comprises polyethylene terephthalate (PET) with a hydrophilic coating on the second side 343 and venting holes 311.

The second layer 344 is positioned below the first layer 341 on the second side or assay facing side of the first layer 341. The second layer 344 itself can be a combination of one or more layers as illustrated in FIG. 3. Regardless of whether the second layer is comprised of one layer or more than one layer, the second layer essentially defines the shape and size of channel in the metering stack, including any receiving chambers that may be part of the channel. For example, the second layer 344 can be formed from one or more layers of polymeric material cut to define the volume and shape of the channel 310 that can contain the target analyte. Other non-limiting methods of forming the channel 310 include injection-molding, stamping, machining, casting, laminating, and 3-D printing. Combinations of such fabrication techniques are also expressly contemplated by the present disclosure. In the embodiment shown in FIG. 3, second layer 344 has a first side 347 facing the first layer 341 and an opposite, second side 348 that faces the assay stack. Furthermore, second layer 344 comprises adhesive layer 345 and plastic layer 346. Adhesive layer 345 fastens the first layer 341 to plastic layer 346. In some embodiments, the second layer 344 can be a combination of one or more plastic layer(s) 346 and adhesive layers 345. Preferably, adhesive layer 345 or plastic layer 346 or both are fabricated from materials which present a hydrophilic surface to the interior surfaces of the channel 310 in order to facilitate the distribution of the target analyte within channel 310. In some embodiments, the hydrophilic plastic sheet(s) can include a PET material with a channel 310 cut into it. If desired, channel 310 may include one or more receiving chambers as shown in FIG. 3. Thus, the thickness and geometry of channel 310 can control the volume of sample to be collected. The hydrophilic interior surfaces of the channel 310 allow the metering stack to collect blood sample by capillary force. In some embodiments, the first layer 341 and the second layer 344 can be one integrated layer used in the metering stack 304.

In FIG. 3, third layer 349 can be formed from a hydrophobic adhesive layer. Non-limiting examples of suitable materials for fabricating third layer 349 include 3M 200MP adhesive or 3M 300MP adhesive (3M, Oakdale, Minn.). In preferred embodiments, the same channel geometry as channel 310 is cut into the third layer to match channel 310 cut in the second layer. In some embodiments, the third layer 349 can have a first side 351 facing the second layer 344 and a second side 352. In some embodiments, the third layer 349 can define the hydrophilic region in a fourth layer 350 positioned below or on the second side 352 of the third layer.

In some embodiments, the fourth layer 350 can be a hydrophilic mesh or porous material. In some embodiments, substantially all of the fourth layer 350 can include the mesh or porous material as shown in FIG. 3. In other embodiments, the hydrophilic mesh or porous material can be a portion of the fourth layer 350. In some embodiments, such as the example shown in FIG. 3, the fourth layer 350 can have a first side 353 facing the third layer 349 and an opposite assay stack-facing second side 354. The hydrophobic third layer 349 can be positioned above the fourth layer 350. The hydrophobic third layer 349 can be a hydrophobic adhesive layer to define a wettable region of the mesh or porous material of the fourth layer 350.

The method used to fabricate the metering stack is not particularly limited, so long as it is compatible with the general manufacturing requirements for medical devices. In certain embodiments, the layers that constitute the metering stack are first fastened together as large multilayer sheet or strip which is then subjected to stamping or cutting processes to form the metering stack, including the channel and any receiving chambers that may be present. In some embodiments, the first layer 341 and second layer 344 can be combined in one piece of plastic material with a hydrophilic surface forming the channel. In some embodiments, the third layer 349 and fourth layer 350 can be combined in one piece of patterned mesh made by printing or other method to define the hydrophilic porous area. In some embodiments, the third layer is not used in the metering stack. Various other combinations of two or more layers, as well as additional layers, are contemplated by various embodiments.

In the binding assay or POC systems of the present disclosure, the assay reactions occur in the assay stack. In general, an assay stack comprises one or more "assay components." As used herein, the term "assay component" refers to one or more of the active component and a passive supporting element or mask, including but not limited to the multiplexed assay pads. The number of assay pads in a particular assay component is not particularly limited and is scalable to meet the assay requirements needed to diagnose the condition of the patients for whom the assay stack is designed. In preferred embodiments, the top layers of the assay pads of a given assay component align vertically with the appropriate regions of the channel in the metering stack above to ensure that a predetermined volume of a biological fluid, sufficient to perform the assay associated with the particular target analyte of interest, is delivered to the assay pad. The assay pad can act as a wick that draws the sample through the mesh of the metering stack into the assay stack, for example through capillary action, gravity, etc. Therefore, once the metering stack and the assay stack are in contact with or within close proximity to each other, the biological fluid to be analyzed is directed to move into the assay pad, where it may encounter one or more chemical reagents required to perform the assay associated with the particular assay component. If desired, the assay stack may comprise additional layers that contain the chemicals required for the completion of the assay. The number of layers required can depend on the number of chemical reactions that need to take place in order to complete the assay. In various embodiments, layers of the assay stack can be made of variously shaped and variously-sized pads of different porous membrane materials, non-limiting examples of which include nylon, polyethersulphone (PES), nitrocellulose, cellulose filter paper, and glass fiber.

The type of assays that may be formed using the assay systems of the present disclosure are not particularly limited and can be any assay for which the required reagents can be stably incorporated into one or more assay pads and which can cause a change that can be detected by the assay reader. In some embodiments, the assay reactions cause a color change, which may be detected using the colorimetric detection methods as described herein. Still other assay reactions may result in another optical change, a fluorescence change, an electrochemical change, or any other detectable change that may occur in a detection membrane of the assay stack. In certain embodiments, the assays may be porous material-based lateral flow assays, vertical flow assays, and/or a combination of lateral and vertical flow assays. In general, the target analyte is contained within a biological fluid, non-limiting examples of which include blood, plasma, serum, saliva, sweat, urine, lymph, tears, synovial fluid, breast milk, and bile, or a component thereof, to name just a few. In certain preferred embodiments, the biological fluid is blood or a component thereof (e.g., blood plasma). For example, in one embodiment, the assay systems of the present disclosure are useful for providing patients with POC information regarding target analytes in their blood composition. Non-limiting examples of analytes that can be measured in blood include thyroid markers (e.g., T3, free T4, thyroid stimulating hormone, etc.), inflammatory markers (e.g., C-reactive protein, etc.), vitamins (detected via a competitive assay structure), metabolic syndrome markers, glucose, glycated hemoglobin, glycated albumin, and serological levels of antibodies against a disease (detected by a labeled antigen architecture). Non-limiting examples of analyte that can be measured in urine include total protein, leukocyte esterase and myoglobin.

FIG. 4 illustrates an exemplary assay stack 406 according to one embodiment of the present disclosure, where such assay stack 406 can in particular be used as assay stack 226 in the embodiment of FIGS. 2A to 2C. In FIG. 4, the assay stack 406 is formed of multiple layers, including one or more of the layers with active components and a passive supporting element or mask. More specifically, in FIG. 4, assay stack 406 comprises assay stack cover layer 410 that features a cut-out portion 411 that is aligned with the channel in the overlying assay stack. Generally, assay stack cover layer 410 is fabricated from a polymeric material that provides rigidity to the assay stack and provides ease of handling during manufacturing of the cartridge. Furthermore, the cut-out portion 411 allows the biological fluid to flow past the assay stack cover layer 410 towards the under assay components when the cartridge is inserted into the assay reader, as described herein. As shown, the assay stack 406 comprises a first separation layer 461 (e.g., a plasma separation membrane) which can be the top-most layer facing the metering stack. The first separation layer 461 may be used to separate components of the biological fluid to prevent undesirable components from reaching the underlying assay components. For example, when the biological fluid is blood, the first separation layer 461 may be a plasma separation membrane that prevents erythrocytes from reaching the assay components after the cartridge has been inserted into the assay reader. This is advantageous because the strong spectral absorption by the hemoglobin present in erythrocytes may overwhelm the color changes that occurs at the assay pad after the assay is performed. Such a plasma separation membrane can be made of a variety of materials, non-limiting examples of which include an asymmetric polysulphone membrane, glass fiber, or cellulose. In some embodiments, the fabrication of the plasma separation membrane can include surface treatments for improved wettability and/or other properties. The plasma separation membrane can be one continuous piece of membrane for all of the assay components, or multiple discontinuous pieces of membrane material that may be the same or different (or some combination thereof) for each of the assay pads in the assay component in the assay stack FIG. 4. When the first separation layer 461 is discontinuous, cross-talk between neighboring assays can be prevented. In some embodiments, some of the assay pads of an assay component have a corresponding plasma separation membrane, while other assay pads do not have such a layer. Other additional components utilized in the immunoassay systems contemplated by the present disclosure are discussed in more detail with respect to FIGS. 8A-8F.

In FIG. 4, assay stack 406 includes assay component 420, which features mask support layer 430 with a plurality of cut-outs 431 that are configured to receive and immobilize assay pads 440 (e.g., hydrophobic membranes) when the assay stack 406 is assembled. Preferably, cut-outs 431 are positioned laterally in mask support layer 430 such that each of the assay pads 440 (e.g., separation layers including a low molecular weight cut off membrane, a hydrophobic membrane, or a combination thereof) are aligned with both the channel and the porous or mesh material of the metering stack above in order to receive predetermined volumes of target analyte sufficient to perform the assay reaction associated with the given assay pad. As shown in FIG. 4, in some embodiments, the assay stack 406 can include a second assay component 462 positioned below the first separation layer 461 (e.g., a plasma separation membrane) and first assay component 420. The second assay component 462 comprises a mask support layer 450 with a plurality of cut-outs 451 that are configured to receive and immobilize assay pads 463 when the assay stack 406 is assembled. Preferably, cut-outs 451 are positioned to align assay pads 463 with assay pads 440 (e.g., hydrophobic membranes) such that the biological fluid containing the target analyte will flow from assay pads 440 into assay pads 463. Assay pads 463 (e.g., detection membranes such as but not limited to color generation membranes) may comprise chemical reagents that are necessary to complete the assay reactions that are initiated once the target analyte flows through the assay pads 440 (e.g., hydrophobic membranes) of assay component 420. In some embodiments, assay pads 463 serve as a detection indicator layer that provides information corresponding to the results of the assay performed. For example, assay pads 463 (e.g., color generation membranes) can include a visual indicator, such as a color change, to indicate the results of the assays, although it is to be understood that the detection membranes contemplated by the present disclosure also contemplate fluorescent and electrochemical changes or responses. Furthermore, while assay stack 406 in FIG. 4 contains only two assay components 420 and 462, it should be understood that the assay stack 406 may contain additional assay components with assay pads that are impregnated with the chemical reagents required to complete and/or report the results of a particular assay. For instance, the assay stack 406 can include any number of assay components necessary to perform the analysis of the blood sample. Because some assays require more chemical steps than others, assay components may comprise more non-functional assay pads which only serve to draw the completed assay products to the bottom of the assay stack, where the results may be detected by the assay reader, as described herein.

Assay stack 406 in FIG. 4 also includes an assay bottom layer 470, which is typically fabricated from a polymeric material to provide mechanical strength and ease of handling of assay stack 406 during the manufacturing process. In addition, assay bottom layer 470 typically comprises a plurality of detection ports 471 which are aligned with the assay pads of the assay stack and sized to permit interrogation of the assay results by the assay reader.

Figure 5A:
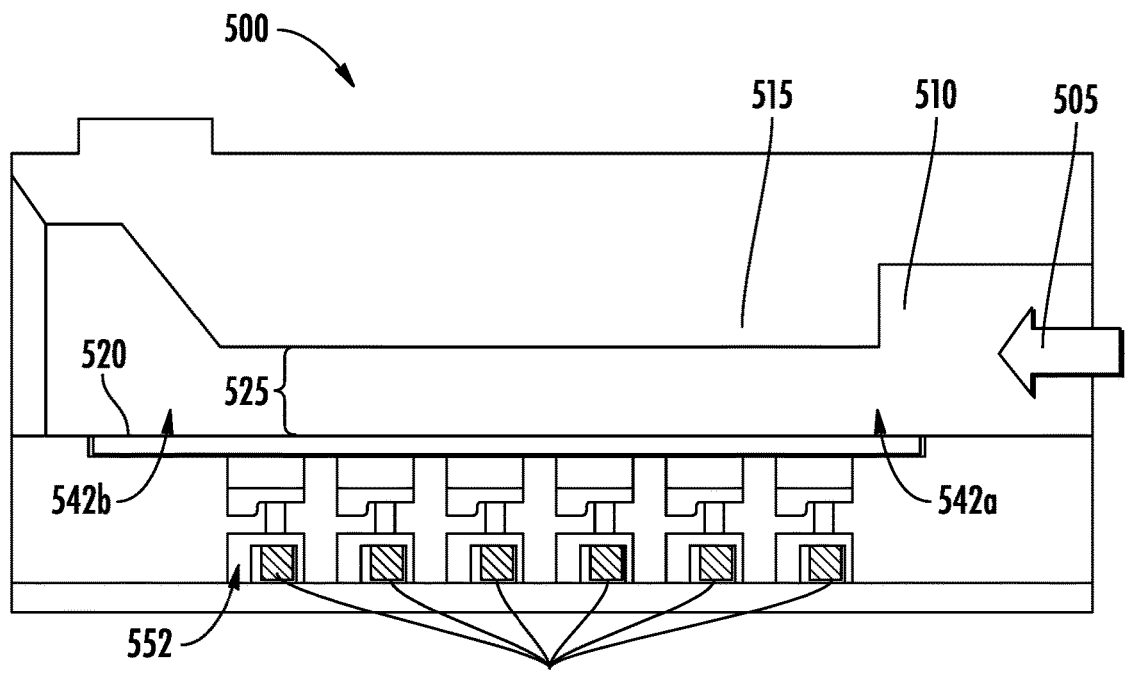
FIG. 5A shows a longitudinal cross-sectional view of an assay reader according to one embodiment of the present disclosure.

FIG. 5A shows a schematic drawing of an assay reader, in longitudinal cross-section, according to one non-limiting embodiment of the present disclosure. In FIG. 5A, assay reader 500 includes cartridge receiving chamber 510 which houses the cartridge when it is inserted as indicated by arrow 505. Tab 515 runs longitudinally along assay reader 500 and extends into cartridge receiving chamber 510. Tab 515 is configured to insert into a slot at the top of the cartridge, such as slot 228 in FIG. 2C, when the cartridge is inserted into the assay reader. In addition, the spacing 525 between the bottom edge of tab 515 and support surface 520 is set such that when the cartridge is inserted, tab 515 compresses the metering stack and the assay stack together, thereby causing the target analyte to flow from the metering stack into the assay stack and initiating the assay reactions. In certain embodiments, the assay reader may comprise a snap-fit mechanism that locks the cartridge in place once it has been fully inserted into the assay reader. This is advantageous because it prevents the user from accidentally removing the cartridge from the assay reader before the assays are complete, which could adversely affect the accuracy of the assay results. In some embodiments, assay reader 500 also comprises sensors 542a and 542b, which detect and time the insertion of the cartridge. For example, as the cartridge is inserted into cartridge receiving chamber 510 and begins to engage with tab 515, the bottom surface of the cartridge may pass over sensor 542a, which is detected by appropriate electronics as the beginning of the insertion of the cartridge. The second sensor 542b is located further inside the assay reader 500 and detects the presence of the cartridge when the cartridge is fully inserted as well as the time at which full insertion occurred. Assay reader 500 may then compare the overall time for insertion of the cartridge to determine if the insertion of the cartridge was timely and proper. In this way, the assay reader will not perform any assay readings in situations where (1) the cartridge was only partially inserted, or (2) the cartridge was partially inserted, removed, and inserted again. Either case could give inaccurate assay readings, due to the incomplete compression of the metering stack and assay stack, resulting in incomplete delivery of the required amount of target analyte to the assay pads in the assay stack.

Figure 5B:
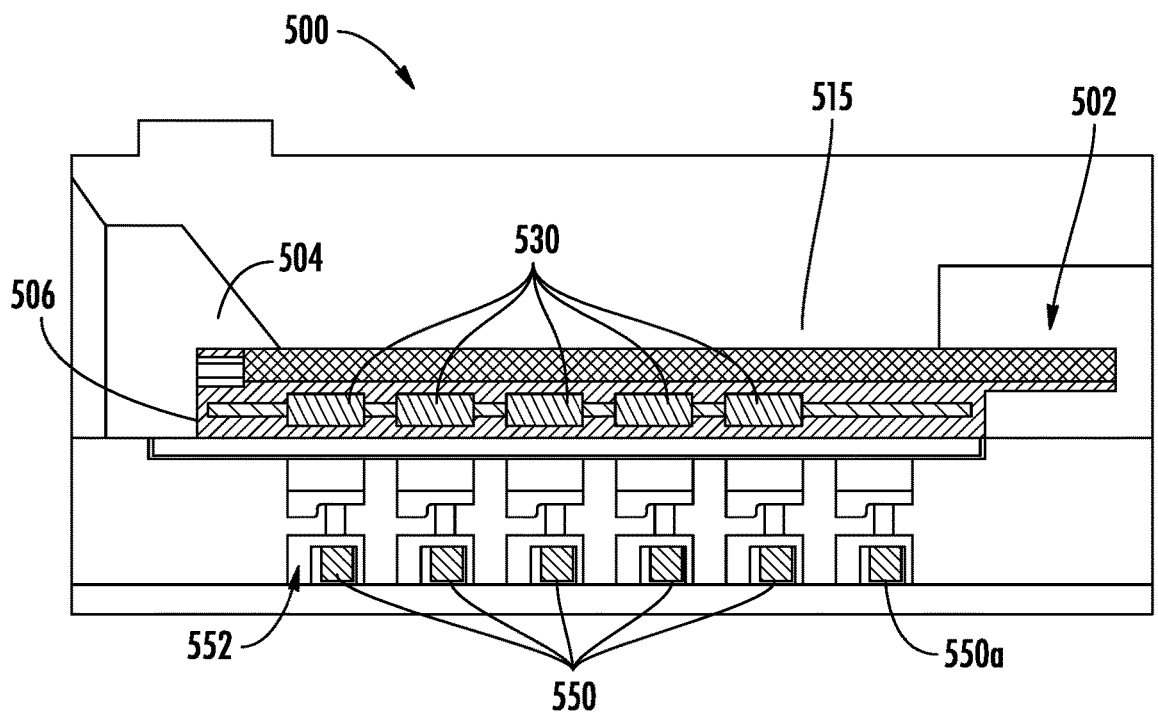
FIG. 5B shows a longitudinal cross-sectional view of an assay reader with an inserted cartridge according to one embodiment of the present disclosure.

In the exemplary embodiment shown in FIG. 5A, assay reader 500 detects the results of the assay by detecting the color change of the assay pad caused by the assay reactions. To achieve this, assay reader 500 comprises a plurality of light sources (not shown in this cross-sectional drawing) and light detection elements 550 arrayed within assay reader 500 such that they align with the assay pads of the cartridge when the cartridge is fully inserted. In order for light detection elements 550 to be able to detect the color of the assay pads, support surface 520 may be equipped with one or more apertures or be fabricated from a transparent material that allows light to penetrate therethrough. However, it is also to be understood that the assay reader 500 can alternatively include components to detect electrochemical or fluorescent changes in a detection membrane portion of the assay stack. Regardless of the changes in the detection membrane that may be measured, the assay reader 500 also includes one or more electromagnets 552 that, when activated, facilitate the transport of the target analyte through the various layers of the assay stack when part of a complex (e.g., an immunocomplex) that includes, inter alia, a magnetic bead as discussed in more detail with respect to FIGS. 8A-8F. FIG. 5B shows a schematic illustration of a longitudinal cross-section of assay reader 500 with cartridge 502 fully inserted. Cartridge 502, which may correspond to cartridge 100 or 200 of FIG. 1 or FIGS. 2A to 2C, includes metering stack 504 and assay stack 506, which are compressed together by tab 515 such that the target analyte is delivered from the metering stack 504 to the assay pads 530. Assay pads 530 are aligned with light detection elements 550. Note, however, that assay reader 500 may include an additional light detection element 550a without a corresponding assay pad 530. The presence of additional light detection elements, such as light detection element 550a, allow the assay reader to be used with different types of cartridges for different assays, particularly cartridges that may be designed to perform more assays, as well as to identify the different types of cartridges for the different assays.

Figure 6A:
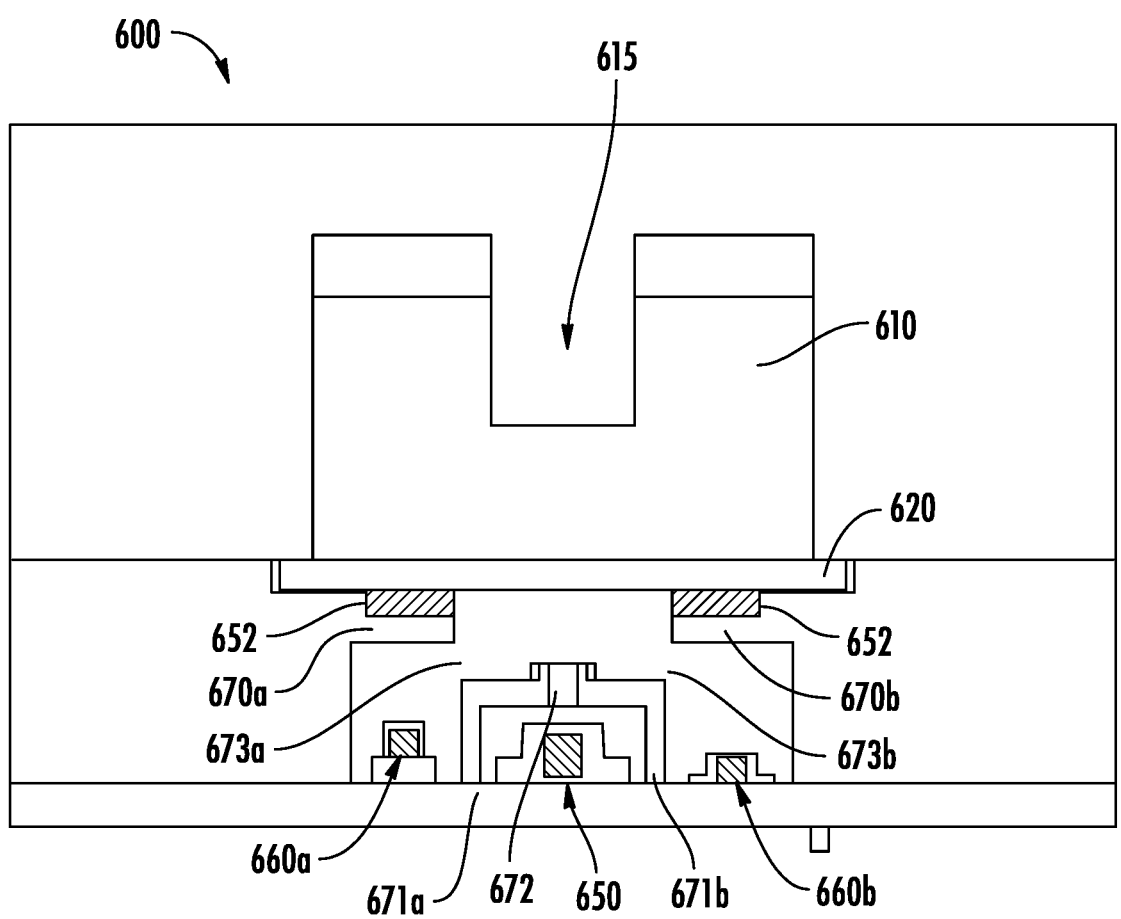
FIG. 6A shows a transverse cross-sectional view of an assay reader according to one embodiment of the present disclosure.

FIG. 6A shows a schematic drawing of a transverse cross-section of the assay reader shown in FIG. 5 in the form of an assay reader 600 that may be used to detect color changes. In FIG. 6A, the assay reader 600 includes a tab 615 that extends into cartridge receiving chamber 610 to engage with a slot on the cartridge. Such engagement then compresses the metering stack and the assay stack against support surface 620, initiating the assay reactions. Light sources 660a and 660b provide light for detecting the assay results and are positioned near light detection device 650. Specifically, as illustrated in FIG. 6A, light sources 660a and 660b provide light to analyze the assay pad corresponding to light detection device 650. In general, it is advantageous to dedicate one or more light sources to each light detection element in order to ensure that the photon flux onto the light detection element is sufficient to obtain an accurate reading. In some embodiments, the light sources dedicated to a particular light detection element have the same output spectrum. In other embodiments, however, the light sources corresponding to a given light detection element produce different output spectra. For instance, the light sources may be light emitting diodes (LEDs) that produce different colors of light. For example, when the target analyte is blood, it may be useful to use light sources that can generate bichromatic pairs (600 nm/570 nm) to detect the presence of undesirable hemolysis. In general, it is advantageous to include optical elements to direct the light and/or reduce the amount of light scattering in the assay reader. In some embodiments, the optical elements are apertures that only allow light emanating from the light source that is line-of-sight to the respective assay pad to reach the assay pad. For example, in FIG. 6A, light source 660a is limited by aperture defining members 670a and 671a such that only the light from light source 660a that passes through aperture 673a will reach the assay pad and subsequently be detected by light detection device 650. Similarly, light source 660b is limited by aperture defining members 670b and 671b, such that only the light from light source 660b that passes through aperture 673b will reach the assay pad and subsequently be detected by light detection device 650. In preferred embodiments, aperture defining members 670a, 670b, 671a, and 671b are fabricated from a black matte material to reduce the amount of undesirable scattering when light sources 660a and 660b are turned on. Furthermore, in this embodiment, light detection device 650 located in a housing that is comprised of aperture defining members 671a and 671b that only permit light that passes through aperture 672 to reach light detection device 650. If desired, the aperture 672 may be fitted with a filter to admit only light of a predetermined wavelength or wavelength range for detection by light detection device 650. This may be useful, for example, when the light sources are equipped to provide only white light for colorimetric analysis. In addition, the light from light sources 660a and 660b and the light to be detected by light detection device 650 may be directed or manipulated using optical elements such as lenses, filters, shutters, fiber optics, light guides, and the like without departing from the spirit and the scope of the present disclosure. The assay reader 600 also includes one or more electromagnets 652 that, when activated, facilitate the transport of the target analyte through the various layers of the assay stack when part of a complex (e.g., an immunocomplex) that includes, inter alia, a magnetic bead as discussed in more detail with respect to FIGS. 8A-8F.

Figure 6B:
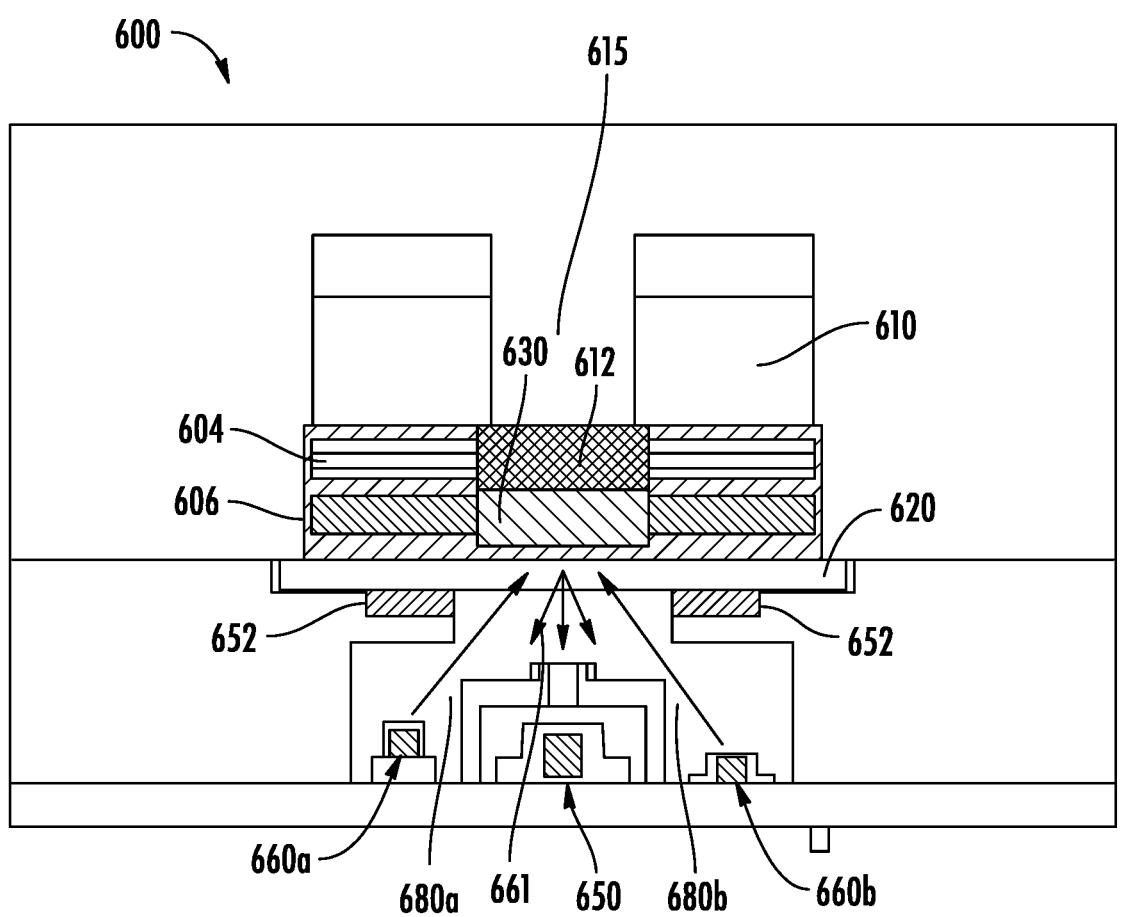
FIG. 6B shows a transverse cross-sectional view of the assay reader with an inserted cartridge according to one embodiment of the present disclosure.

FIG. 6B shows a schematic illustration of the operation of the assay reader described in FIG. 6A. In FIG. 6B, a cartridge comprising metering stack 604 and assay stack 606 are inserted into cartridge receiving chamber 610 of assay reader 600. Tab 615 compresses metering stack 604 and assay stack 606 against support surface 620 to cause the target analyte to flow from the channel 612 into assay pad 630. As noted previously, assay reader 600 may be fitted with sensors to confirm that the cartridge has been inserted correctly and in a timely manner. Assay reader 600 may also be pre-programmed before sample collection, either by the user or during the manufacturing process, to illuminate the assay pads at the appropriate time based on the type of cartridge being used. In this way, assay reader 600 collects assay data from assay pad 630 only when the assay is completed. Alternatively, if desired, assay reader 600 may be configured to collect assay data from assay pad 630 during the entire assay reaction after the cartridge has been inserted. As shown in FIG. 6B, light source 660a provides light beam 680a, which impinges on the bottom face of assay pad 630 to produce reflected light beam 661. Similarly, light source 660b produces light beam 680b, which may impinge on the bottom of the assay pad 630 to produce reflected light beam 661 at the same time as light source 660a or a different time, depending on the requirements of the assays being detected.

Figure 7:
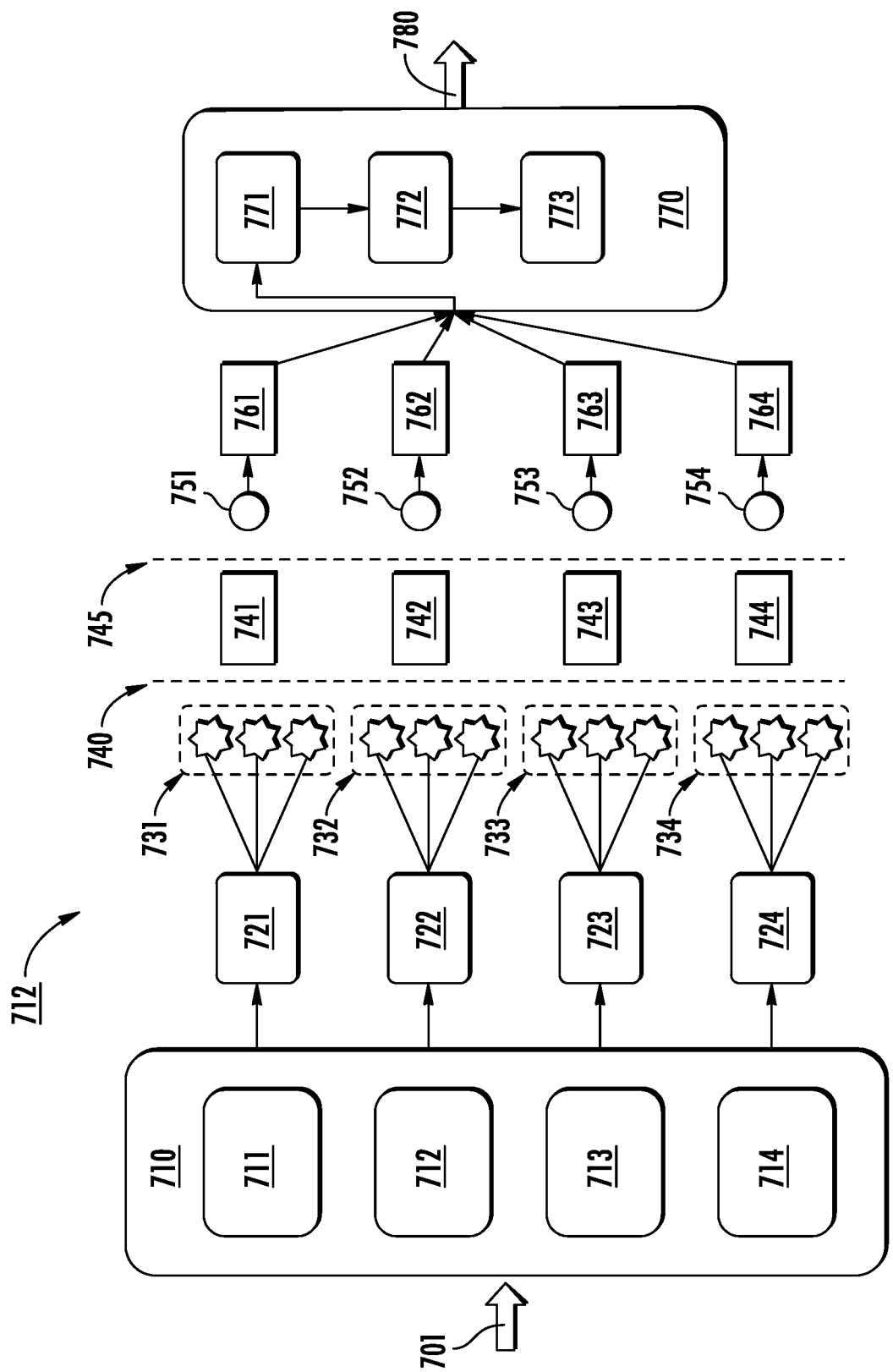
FIG. 7 shows a block diagram of the sensor system of the assay reader, according to an exemplary implementation of the present disclosure.

FIG. 7 shows a block diagram 700 of a sensor configuration inside an assay reader according to one exemplary embodiment of the present disclosure. In FIG. 7, four assay pads (identified by reference numerals 741, 742, 743, and 744) have completed their assay reactions with the target analyte, undergone the respective color changes, and are ready for colorimetric analysis. Note that, if desired, this configuration can also be used to collect data from the four assay pads to monitor the progress of the assay reactions. Input signal 701 from a first microcontroller serial-peripheral interface bus (MCU SPI Bus) enters digital-to-analog converter unit 710, which comprises individual digital-to-analog converters 711, 712, 713, and 714 that independently control current sources 721, 722, 723, and 724. These current sources, in turn, power light sources 731, 732, 733, and 734, respectively. In some embodiments, input signal 701 may be sent by a timing circuit at a predetermined time after the insertion of the cartridge into the assay reader. In such embodiments, the predetermined time corresponds to the known time or times for the assay reactions in the assay pads to reach completion. In some preferred embodiments, the light sources 731, 732, 733, and 734 are activated at the same time to measure the assay-induced color change of assay pads 741, 742, 743, and 744 simultaneously in a multiplexed mode. However, this present disclosure also contemplates operating all of the light sources separately and sequentially, or some simultaneously and some separately, depending on the timing requirements of the assays in the cartridge.

In this non-limiting example, each of light sources 731, 732, 733, and 734 includes individual three light emitting diodes (LEDs) which may be the same or different colors, depending on the requirements of the assay and any optical elements that may be present in the assay reader. For example, in certain embodiments, the three LEDs in a particular light source (e.g., 731) may be red, green, and blue (RGB LEDs), such that the light impinging on the assay pad is white light when all three LEDS are activated. Of course, the light sources are not limited to any particular number or type of LEDs or other light generating devices. More generally, the light sources that are useful in the assay readers of the present disclosure are not particularly limited, so long as they provide light of suitable wavelength(s) and brightness for the light detection element to make an accurate reading of the colored light reflected from the assay pad. In certain non-limiting embodiments, the light sources are light emitting diodes (LEDs), organic light emitting diodes (OLEDs), active matrix organic light emitting diodes (AMOLEDs), or lasers. For example, the light source may be only one LED that has sufficient brightness and the proper wavelength to allow colorimetric analysis of an assay reaction in a given assay pad. In certain embodiments, the light sources may produce light of specific wavelengths. As one non-limiting example, when the biological fluid containing the target analyte is blood (with erythrocytes removed), a bichromatic light source that produces light at 570 nm and 600 nm may be used to detect the presence of heme on a non-functional (i.e., assay reagent-free) assay pad, which is indicative of undesirable hemolysis in the patient. Alternatively, the light source may be a broadband source that is paired with one or more narrow bandpass filters to select light of certain desired wavelength(s). Typically, the light sources produce light in the visible region of the electromagnetic spectrum (i.e., wavelength between 400-700 nm) although this present disclosure also contemplates light sources that produce electromagnetic radiation in the infrared (700 nm to $10^6$ nm) or ultraviolet regions (10 nm-400 nm) of the electromagnetic spectrum, so long as they are paired with the appropriate light detection devices. Combinations of different light sources are also expressly contemplated by the present disclosure.

In FIG. 7, element 740 is a schematic representation of optical elements that optionally may be present in the optical path between the light sources 731, 732, 733, and 734 and assay pads 741, 742, 743, and 744. When desired, one or more optical elements may be located between the light source and its corresponding assay pad to direct the light, focus the light, reduce undesirable scattering, select one or more wavelengths for assay detection, or some combination thereof. Non-limiting examples of such optical elements include apertures, lenses, light guides, bandpass filters, optical fibers, shutters, and the like. Similarly, element 745 represent optical elements that optionally may be present in the optical path between assay pads 741, 742, 743, and 744 and corresponding light detection devices 751, 752, 753, and 754. These optical elements may be used to manipulate the light upstream of the light detector devices in a manner similar to that described for element 740. It is to be understood that different types and numbers of optical elements may be used for each combination of light source, assay pad, and light detection device. Light detecting devices 751, 752, 753, and 754 detect the light from the assay pads 741, 742, 743, and 744. In this non-limiting example, the light detecting devices are photodiodes. More generally, the type of light detection device is not particularly limited, provided that it is capable of detecting the light that is reflected from the assay pads used for colorimetric measurement of the assay results. Other examples of suitable light detection elements include photodiode arrays, CCD chips, and CMOS chips. The outputs from light detection devices (e.g., photodiodes) 751, 752, 753, and 754 are sent to transimpedance amplifier/low pass filter elements 761, 762, 763, and 764, which convert the current signal from the photodiodes to a voltage output, while filtering unwanted signal components. The output from transimpedance amplifier/low pass filter elements 761, 762, 763, and 764 are sent to analog-to-digital converter unit 770, which comprises multiplexer unit 771, gain 772, and analog-to-digital converter 773. The output of analog-to-digital converter unit 770 may be sent to a component 780, which may be a second MCU SPI bus, a transmitter, or a processor. In certain embodiments, the transmitter allows for hardwired or wireless connectivity (e.g., Bluetooth or Wi-Fi) with a personal computer, mobile device, or computer network. In one particularly useful embodiment, the assay results are transmitted to the user's mobile device or personal computer, where they are displayed in a graphical user interface (GUI). If desired, the GUI may display prior assay results, in addition to the current results, in order to provide the user with information regarding the overall trends in the results of the assays. For example, if the user is diabetic, the GUI may plot the glucose levels measured by the assay reader as a function of time to allow the user to determine whether blood glucose level is being properly controlled. In addition, the assay results may be transmitted from the user's mobile device or computer to a computer network, such as one belonging to the user's physician. In this way, the assay systems of the present disclosure can allow a user's physician to monitor a patient closely, by providing up-to-date medical information from the assay results obtained by the assay reader.

It should be noted that the optical detection systems described in the foregoing correspond to some exemplary embodiments of the system, but that the present disclosure expressly contemplates other types of detection systems as well. In general, any detection system which corresponds to a signal change caused by an assay reaction may be used in connection with the assay reader of the present disclosure. Thus, for example, in certain embodiments, the detection system is an optical detection system that is based on chemiluminescence. In such embodiments, light sources such as LEDS and OLEDS are not required to detect a color change caused by the assay reaction in the assay pads. Rather, the signal change may be caused by the reaction of an oxidative enzyme, such as luciferase, with a substrate which results in light being generated by a bioluminescent reaction. In another exemplary embodiment, the signal change caused by the assay reaction may be detected by electrochemical reaction.

FIGS. 8A-8F illustrate a further embodiment of cartridges 100, 200, or 502 in the form of a cartridge 800 that includes a metering stack 802 and an assay stack 804 during various stages of performing an immunoassay after a fluid sample 814 to be analyzed for the presence of a target analyte 816 has been introduced to the cartridge 800. The metering stack 802 is configured to receive and distribute the target analyte 816 along a channel, where the channel has a bottom that comprises a porous or mesh material and one or more venting holes in communication with the channel, as described in detail above. As also described above, a spacer material is disposed between the metering stack and the assay stack, wherein the spacer material provides a gap between the metering stack and the assay stack that prevents the target analyte from flowing from the metering stack into the assay stack when the cartridge is in an uncompressed state. Additionally, the porous or mesh material permits the target analyte 816 to flow from the metering stack 802 to the assay stack 804 upon compression of the cartridge 800.

Once introduced to the metering stack 802, the fluid sample 814 containing the target analyte 816 passes to the first separation layer 806, and ultimately, the target analyte 816 reaches a detection membrane 812 (e.g., a color generation membrane) via a second separation layer 808 (e.g., a hydrophobic membrane, a low molecular weight cut-off membrane, or a combination thereof) as discussed in more detail below. When the fluid sample 814 is blood, the first separation layer 806 can be referred to as the plasma separation membrane. Further, when the fluid sample 814 is blood, the first separation layer 806 can include pores 840 that have a pore size large enough to allow the target analyte 816 to be pulled through additional layers of the cartridge 800 but that also have a pore size small enough (e.g., less than about 2 micrometers) to prevent passage of any erythrocytes through additional layers of the cartridge 800, which could affect the accuracy of the assay results. This is because there is a strong spectral absorption by the hemoglobin present in erythrocytes that may, for example, overwhelm the color changes that occur after the assay is performed.

Figure 8A:
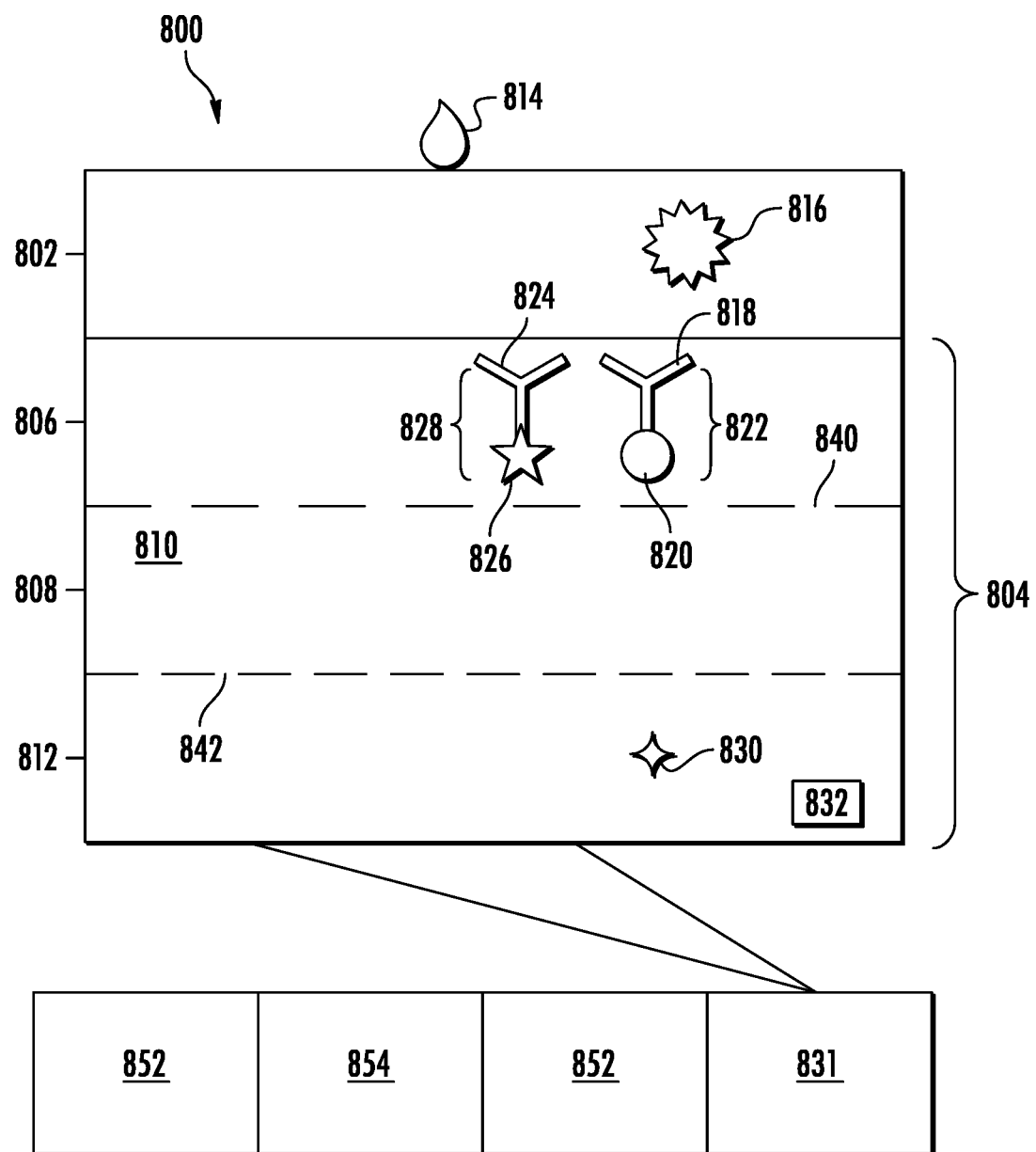
FIGS. 8A-8F illustrate a cartridge that includes a metering stack and an assay stack during various stages of the immunoassay process following the introduction to the cartridge of a fluid to be analyzed for the presence of a target analyte.
Figure 8B:
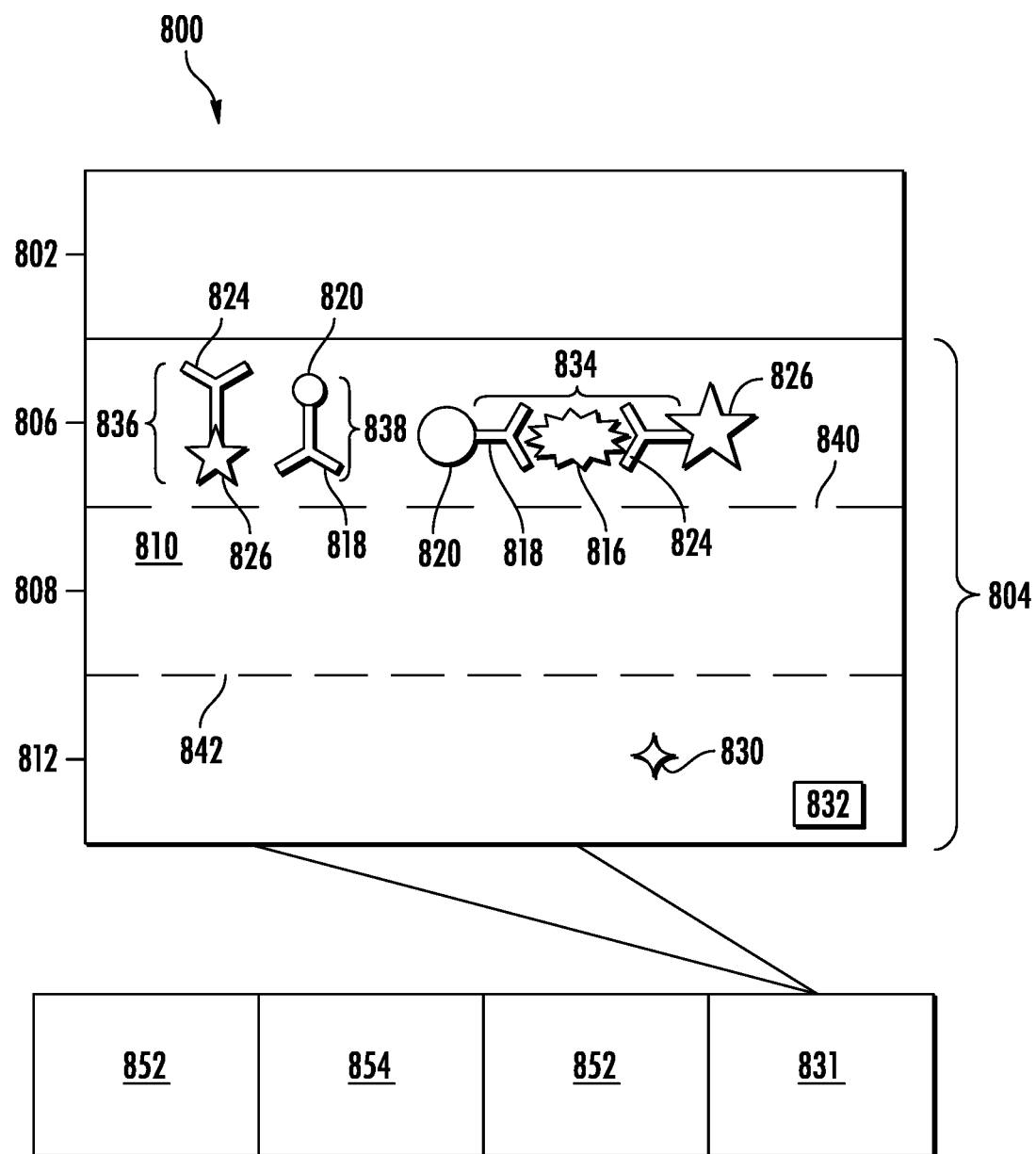
Figure 8C:
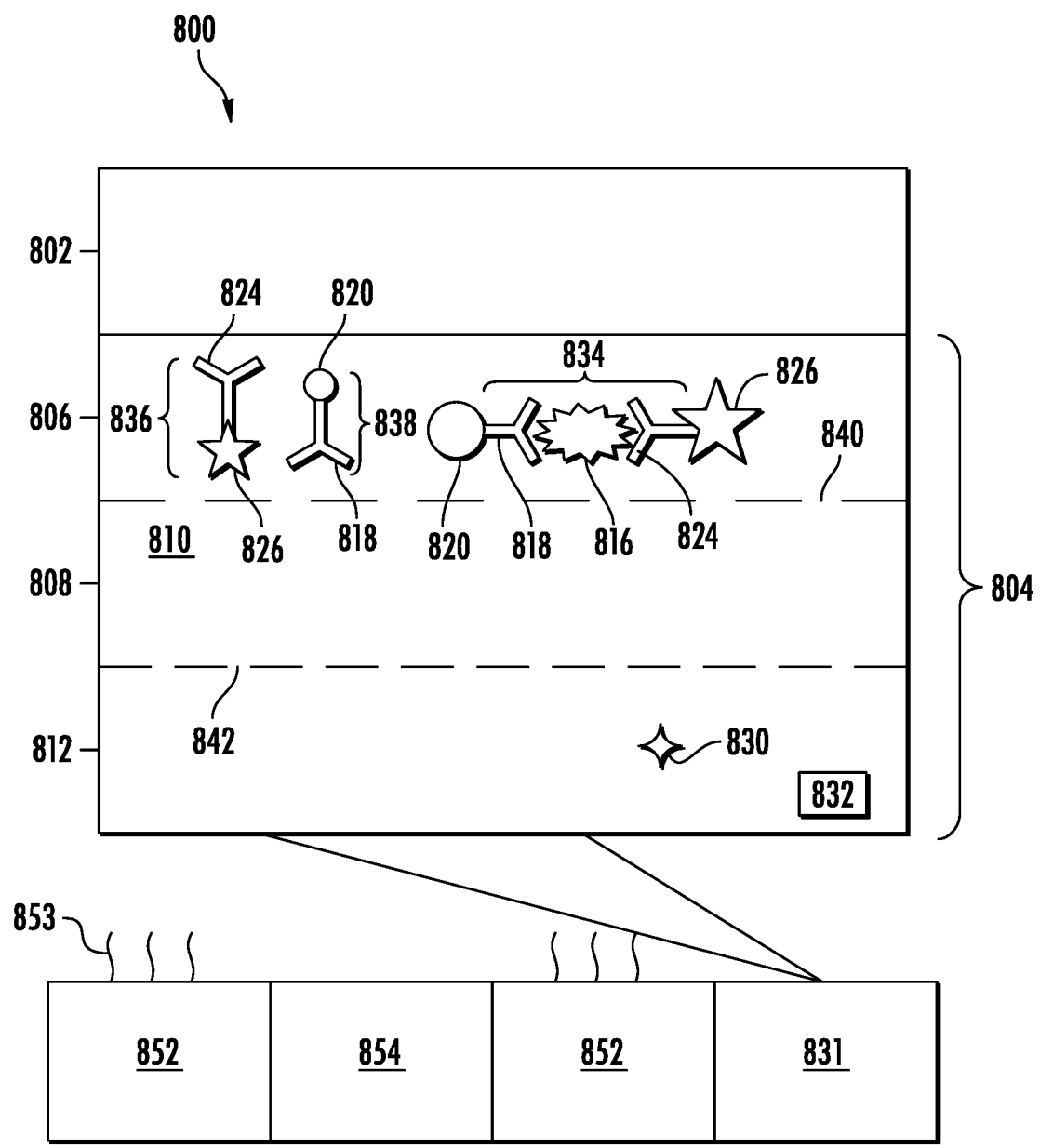
Figure 8D:
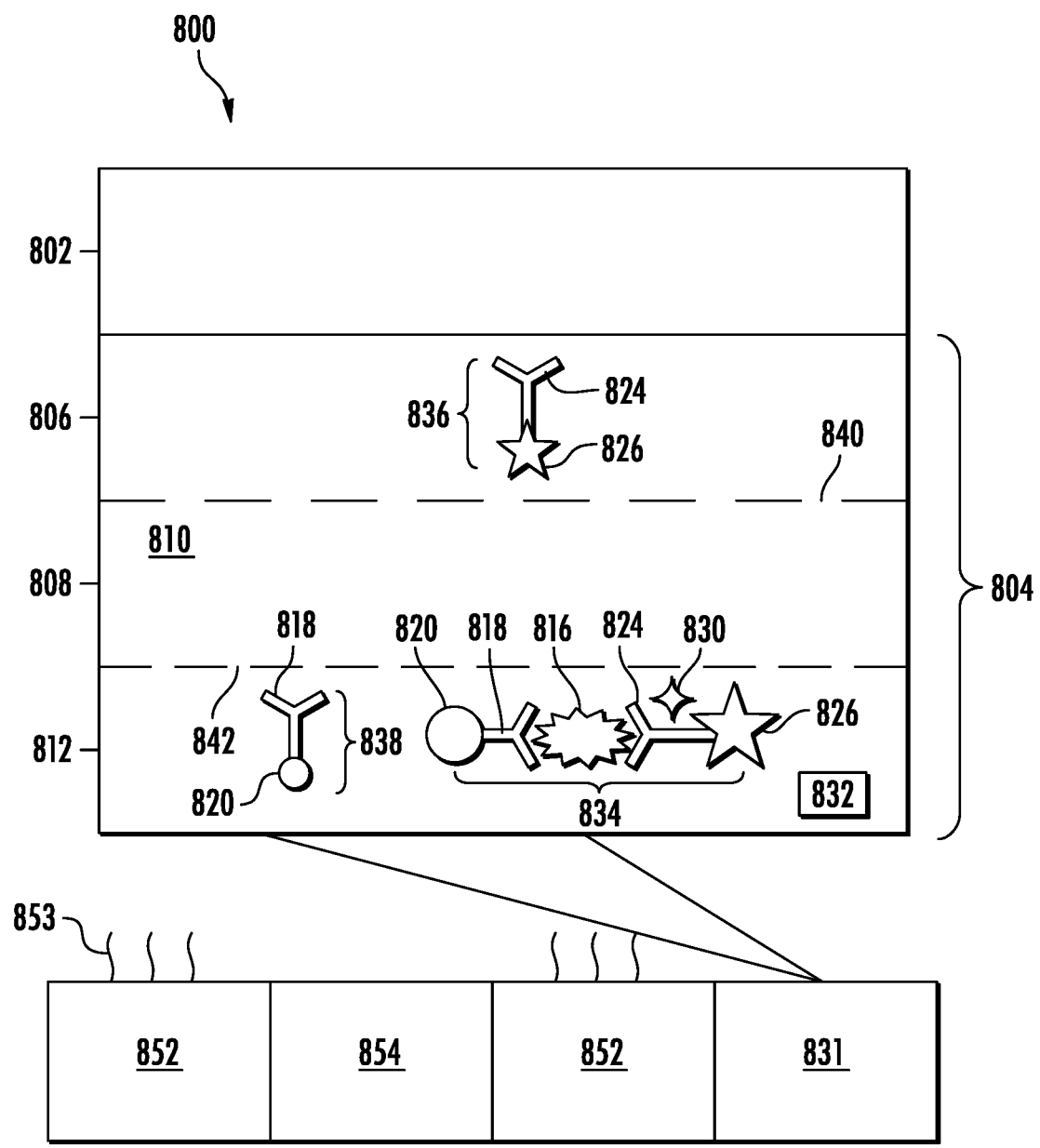

Additionally, as shown in FIG. 8A, the first separation layer 806 may also include a plurality of first complexes 822 that each include a capture molecule 818 (e.g., a capture antibody in the case of an immunoassay) and a magnetic bead 820 that are conjugated and a plurality of second complexes 828 that each include a detection molecule 824 (e.g., a detection antibody in the case of an immunoassay) and a detection label 826 that are conjugated. Ultimately, as shown in FIG. 8B, any target analyte 816 present in the fluid sample 814 can join to the plurality of first complexes 822 and the plurality of second complexes 828 to create a third complex 834 (e.g., an immunocomplex in the case of an immunoassay) that can be pulled through the assay stack 804 upon activation of an electromagnet 852, causing the electromagnet 852 to emit an electromagnetic force or signal 853 (see FIGS. 8C and 8D), where the specific structure and components of the first separation layer 806 essentially replace the wash and incubation steps that are typically employed in a standard assay, although it is to be understood that the complexes may be located on a different layer besides the first separation layer 806 in some embodiments, where washing and incubation steps would still be eliminated. In any event, regardless of where the first complexes 822 and the second complexes 828 are initially deposited on the assay stack 804, the need for physical washing with fluid or complex moving parts is eliminated in the assay system contemplated by the present disclosure. The electromagnet 852 may be part of an assay reader as previously discussed in connection with FIGS. 1 and 5A to 7.

The capture molecule 818 can be a capture molecule (e.g., a capture antibody in the case of an immunoassay) that specifically binds to the target analyte 816. Capture molecules 818 for a target analyte 816 are readily known by one having ordinary skill in the art and may be produced by routine techniques or are readily available commercially. Further, the magnetic beads 820 to which the capture molecules 818 are coupled can be ferromagnetic particles which are readily conjugated to biomolecules such as the capture molecule 818. The magnetic beads 820 can have a diameter ranging from about 10 nanometers to about 10 micrometers, such as from about 20 nanometers to about 7.5 micrometers, such as from about 30 nanometers to about 5 micrometers. Suitable magnetic beads are well known by one having ordinary skill in the art and are available from commercial suppliers. The magnetic beads 820 can include iron oxide particles, such as magnetite ($Fe_3O_4$), although it is to be understood that any other iron oxide particles can be used so long as the magnetic beads 820 have superparamagnetic properties in that the beads exhibit magnetic behavior only in the presence of an external magnetic field. This property is dependent on the small size of the particles in the magnetic beads 820 and enables the magnetic beads 820 to be separated in suspension, along with the capture molecules 818 to which the magnetic beads 820 are coupled. Since the magnetic beads 820 do not attract each other outside of a magnetic field, the magnetic beads 820 can therefore be used without any concern about unwanted clumping. The capture molecule 818 can be coupled to the magnetic bead 820 directly or indirectly via a linker molecule that can be bound to the capture molecule 818 and the magnetic bead 820 either covalently or non-covalently. In any event, suitable methods for forming the first complex 822 containing the capture molecule 818 (e.g., a capture antibody) and the magnetic bead 820 are well known by one having ordinary skill in the art.

Further, like the capture molecule 818, the detection molecule 824 (e.g., the detection antibody in the case of an immunoassay) is also a molecule that specifically binds to the target analyte. Detection molecules 824 for a target analyte 816 are readily known by one having ordinary skill in the art and may be produced by routine techniques or are readily available commercially. The detection molecule 824 is linked to the detection label 826. The detection label 826 can begin a chemical reaction with the reagent or substrate 830 located in the detection membrane 812 (e.g., a color generation membrane, a fluorescence generation membrane, an electrochemical signal generation membrane, etc.) to produce a detectable signal as discussed in more detail below. For example, the detection label 826 may catalyze the oxidation of the substrate 830. The oxidized form of the substrate 830 may then provide a detectable signal in the form of a color change, a fluorescence change, or an electrochemical change. Suitable detection labels 826 are well known in the art and can include peroxidase, glucose oxidase, and alkaline phosphatase. In one particular embodiment, the detection label 826 can be a peroxidase enzyme, such as horseradish peroxidase (HRP) or, in another embodiment, the detection label 826 can be β-galactosidase. The detection molecule 824 can be coupled to the detection label 826 directly or indirectly via a linker molecule that can be bound to the detection molecule 824 and the detection label 826 either covalently or non-covalently. In any event, suitable methods for forming the second complex 828 containing the detection molecule 824 (e.g., a detection antibody) and the detection label 826 are well known by one having ordinary skill in the art. In addition, it should be understood that when the assay is a sandwich assay, the capture molecule 818 and the detection molecule 824 can be selected specifically for the target analyte 816 and are paired to ensure that different epitopes of the target analyte 816 are targeted so that both molecules can bind to the target analyte 816 to create a complex 834 that includes the capture molecule 818, the detection molecule 824, and the target analyte 816 (along with the magnetic bead 820 and the detection label 826). Further, it should also be understood that other assay architectures fall within the scope of the present disclosure, such as, but not limited to competitive and labelled-antigen architectures.

The assay stack 804 also includes a second separation layer 808 (e.g., a hydrophobic membrane, a low molecular weight cut-off membrane, or a combination thereof) that is positioned adjacent to the first separation layer 806. The second separation layer 808 can include pores 842 having a pore size large enough to allow for the third complex 834 comprising the target analyte 816 bound to one of the first complexes 822 and one of the second complexes 828 to pass to the detection membrane 812 in the presence of an activated electromagnet 852. The second separation layer 808 can also include pores 842 having a pore size small enough to prevent passage of any unbound second complexes 836 to the detection membrane 812 (see FIGS. 8B-8F) in the presence of an activated electromagnet 852, where the passage of such unbound second complexes 836 could decrease the accuracy of the assay since excess detection labels 826 that are not coupled to a target analyte 816 as part of the third complex 834 could be allowed to pass through to the detection membrane 812 and potentially interact with the substrate 830, which could result in the assay indicating the presence of higher concentrations of the target analyte 816 in the fluid sample 814 than is actually present. Further, it is to be understood that the passage of unbound first complexes 838 to the detection membrane 812 in the presence of the activated electromagnet 852 is acceptable as the unbound first complexes 838 do not include detection labels 826.

In some embodiments, the pores 842 can have a pore size that has a molecular weight cut-off of about 150,000 Daltons or less, such as about 125,000 Daltons or less, such as about 100,000 Daltons or less, to prevent the passage of the unbound second complexes 836 containing the detection molecule 824 and the detection label 826 through the pores 842 as the molecules (e.g., antibodies) can have a molecular weight of about 150,000 Daltons or more. Moreover, it is to be understood that although the first complexes 822 also include molecules (e.g., antibodies) that may have a molecular weight above about 150,000 Daltons or more (e.g., capture molecules 818), the presence of the magnetic beads 820 in the first complexes 822 upon activation of the electromagnet 852 provides sufficient force to allow the second complexes 828 to pass through the second separation layer 808 to the detection membrane 812.

In addition to the pore size of the second separation layer 808, the second separation layer 808 can also include a hydrophilic treatment 810 (e.g., a coating) that can be applied in order to tune the second separation layer 808 so that it has the desired molecular weight cut-off based on the specific detection molecules 824 utilized in the second complexes 828. In one embodiment, the hydrophilic treatment 810 can include one or more surfactants. Any suitable surfactant known by one of ordinary skill in the art can be utilized to form the hydrophilic treatment 810, including, but not limited nonionic surfactants (e.g., surfactants having a hydrophilic polyethylene oxide chain and an aromatic hydrocarbon lipophilic group such as Triton X-100, surfactants containing polysorbate molecules containing a hydrophilic head group of oligo(ethylene glycol) chains and a hydrophobic tail of fatty acid ester moiety such as Tween 20, Tween 40, and Tween 80, etc.), anionic surfactants (e.g., sodium laureth sulfate, sodium dodecyl sulfate, etc.), and cationic surfactants (e.g., methyl triethanolammonium). In any event, it is to be understood that the combination of low molecular weight cut-off membrane materials, hydrophobic membrane materials, hydrophilic treatments or coatings, etc. to form the second separation layer 808 can be optimized by one of ordinary skill in the art based on the magnetic field strength of the electromagnet signal 853 of the electromagnet 852, the size of the magnetic beads 820, and the molecular weight cutoffs of the materials utilized.

Figure 8E:
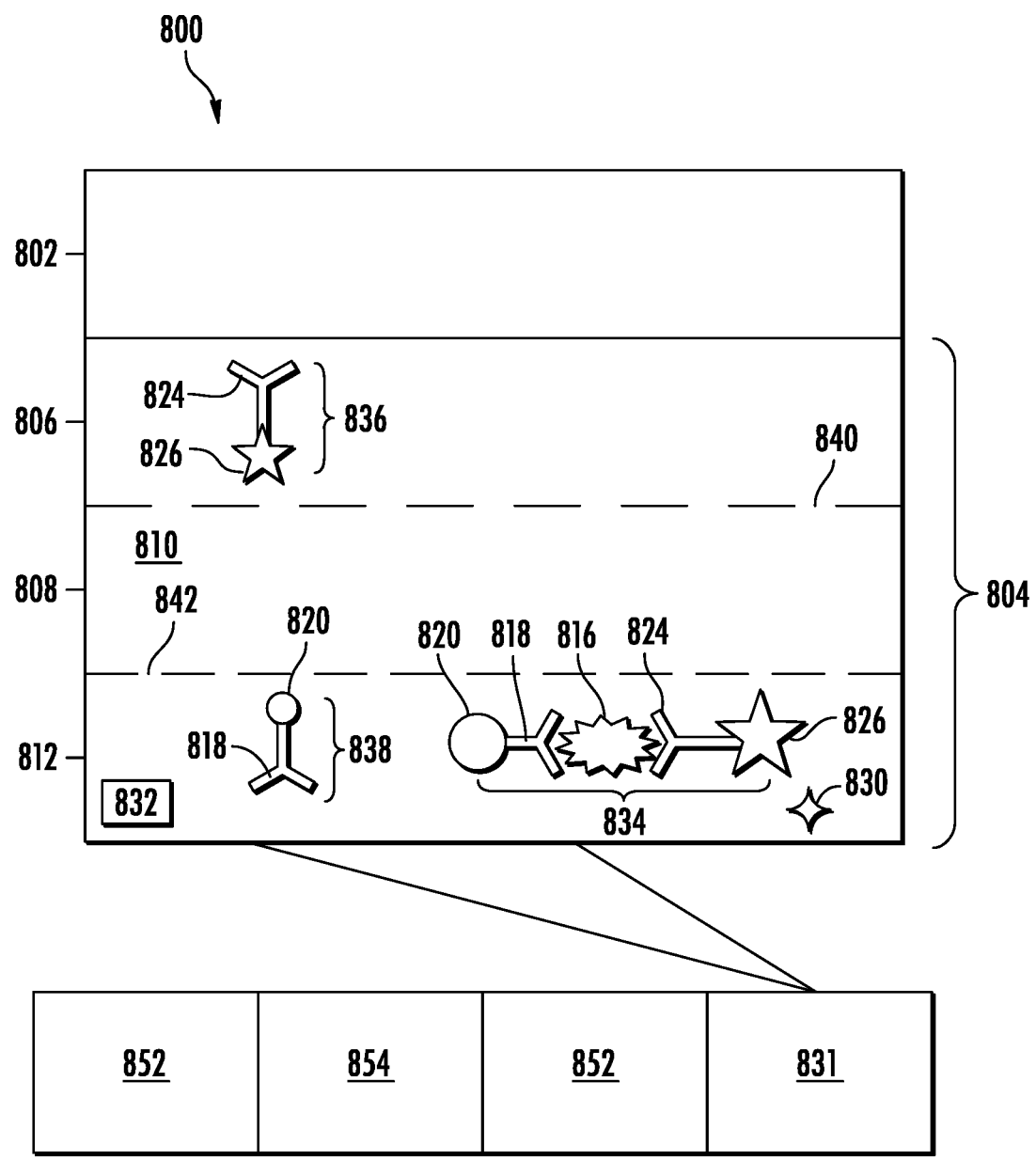
Figure 8F:
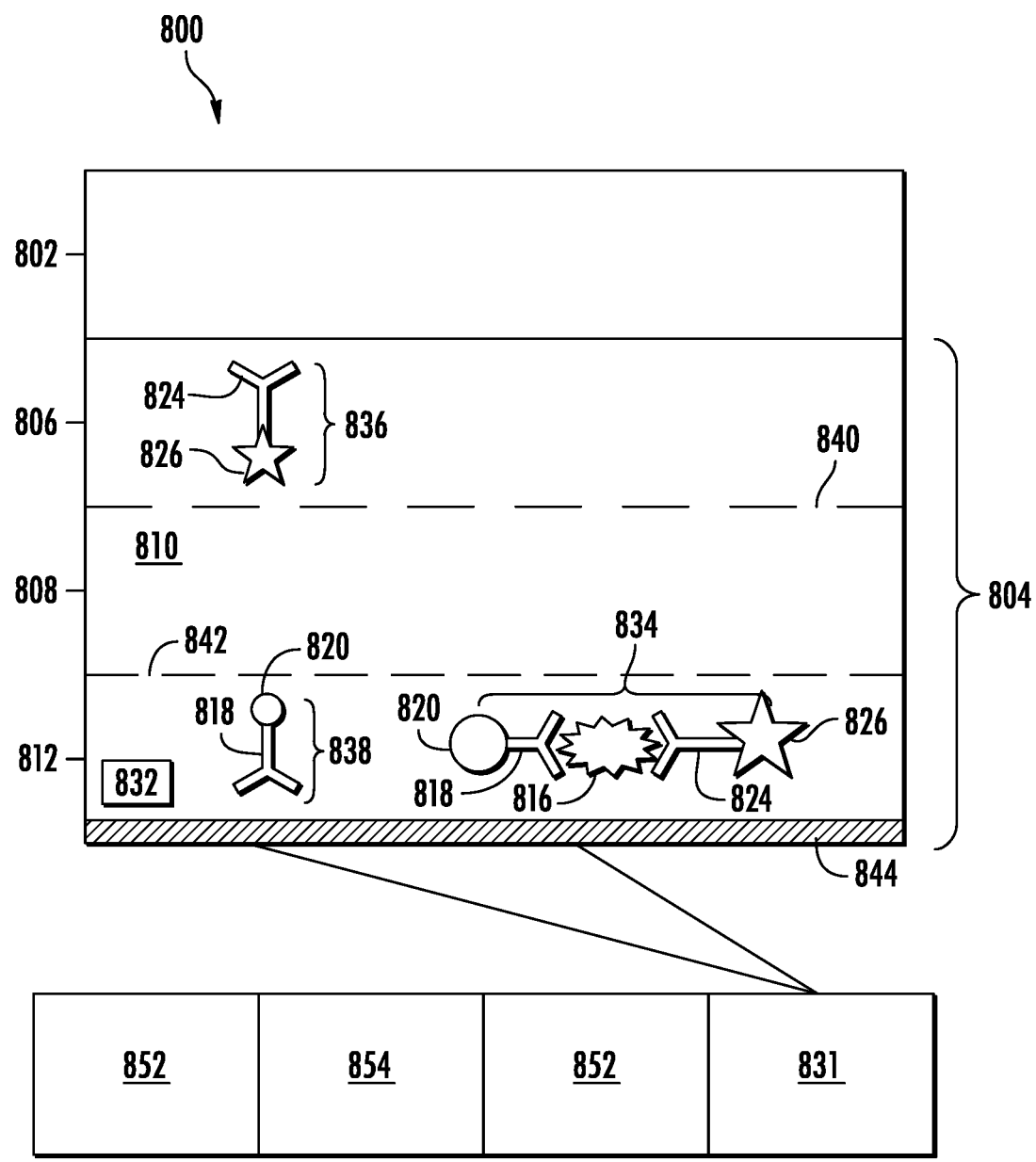

After any formed third complexes 834 containing any target analyte 816 present and sandwiched between a first complex 822 and a second complex 828 as well as any unbound first complexes 838 containing a capture molecule 818 and a magnetic bead 820 pass through the pores 842 in the second separation layer 808 in response to a magnetic force or signal 853 emitted by one or more electromagnets 852, the detection labels 826 in each of the third complexes 834 can react with the substrate 830 present in the detection membrane 812. See FIGS. 8D-8F. The reaction between the substrate 830 and any detection label 826 present can elicit a quantifiable response 844 (e.g., a colorimetric response, a fluorescent response, an electrochemical response, etc.) in the presence of the target analyte 816, wherein the quantifiable response 844 corresponds to an amount of detection molecule 824 present in the detection membrane 812 as shown in FIGS. 8E and 8F. Further, the amount of detection molecule 824 present in the detection membrane 812 corresponds to an amount of the target analyte 816 present in the fluid sample 814. In one embodiment, the substrate 830 can include one or more reagents for the detection label 826. For example, in one embodiment, the substrate 830 can include one or more reagents which are catalyzable by the detection label 826 attached to the detection molecule 824 to provide a detectable signal within the detection membrane 812. For instance, the substrate 830 can include a first reagent and/or a second reagent, where the second reagent can be oxidizing agent or a precursor thereof for the first reagent. Further, a reaction between the first reagent and the oxidizing agent can be catalyzable by the detection label 826 to provide a detectable signal in the detection membrane 812.

The choice of first and second reagents can depend on the detection label 826 that is part of the second complex 828. The first reagent may be reactable with the second reagent in the presence of the detection label 826. Suitable first reagents can include tetramethylbenzidine (TMB), alpha guaiaconic acid, 2,2'-azino-bis(3-ethylbenzothiazolidine-6-sulphonic acid), hydroquinone, phenylenediamine, o-dianisidine, o-tolidine (dimethylbenzidine), 6-methoxyquinoline, and 3,3'-diaminobenzidine, 3-amino-9-ethylcarbazole, or a combination thereof. The second reagent can be an oxidizing agent or a precursor thereof and can be reactable with the first reagent in the presence of the detection label 826. Suitable second reagents for the detection of a detection label 826 that includes peroxidase can include hydrogen peroxide or a precursor thereof. For example, the second reagent can include urea peroxide or sodium perborate. Therefore, the first reagent can be a compound that reacts with hydrogen peroxide in the presence of the peroxidase detection label 826. Further, suitable second reagents for the detection of a glucose oxidase detection label 826 can include glucose or a precursor thereof. In some preferred embodiments, the substrate 830 for the detection of a peroxidase detection label 826 can include tetramethylbenzidine (TMB) and perborate (PER). In some embodiments, the substrate 830 can include single reagent (i.e., a first reagent only). A reaction between the reagent and the detection label 826 can provides a detectable signal without the need for a second reagent. This may be useful, for example, in the detection of an alkaline phosphatase detection label 826. Suitable reagents for the detection of alkaline phosphatase include 1-naphthyl-phosphate; 5-bromo-4-chloro-3-indolyl phosphate (BCIP); hydroquinone diphosphate; phenolphthalein phosphate; 4-aminophenyl phosphate; 3-idoxyl phosphate; and phenyl phosphate. However, it should be understood the substrate 830 can include other reagents known to one having ordinary skill in the art based on the particular detection label 826 being utilized.

In any event, the quantifiable response 844 (e.g., a colorimetric response, a fluorescent response, an electrochemical response, etc.) in the detection membrane 812 can be detected by one or more detection devices, which, for example, can include light detection devices 854 as shown in FIG. 8F when the quantifiable response is a color change. Meanwhile, one or more light sources 831 provide light for detecting the quantifiable response 844 (e.g., color change) in the detection membrane 812 (e.g., color generation membrane) and can be positioned near light detection device 864. In the case of a colorimetric response, the one or more light sources 831 provide light to analyze the quantifiable response 844 (e.g., color change) in the detection membrane 812 (e.g., color generation membrane) corresponding to light detection device 854. As described above, it is advantageous to dedicate one or more light sources to each light detection element in order to ensure that the photon flux onto the light detection element is sufficient to obtain an accurate reading. In some embodiments, the light sources 831 dedicated to a particular light detection device 854 have the same output spectrum. In other embodiments, however, the light sources 831 corresponding to a given light detection devices 854 produce different output spectra. For instance, the light sources may be light emitting diodes (LEDs) that produce different colors of light. In general, it is advantageous to include optical elements to direct the light and/or reduce the amount of light scattering in the assay reader. If desired, the light detection device 854 may be fitted with a filter to admit only light of a predetermined wavelength or wavelength range for detection by light detection device 854. This may be useful, for example, when the light sources 831 are equipped to provide only white light for colorimetric analysis. In addition, the light from light sources 831 and the light to be detected by light detection device 854 may be directed or manipulated using optical elements such as lenses, filters, shutters, fiber optics, light guides, and the like without departing from the spirit and the scope of the present disclosure. More generally, the light sources 831 that are useful in the assay readers of the present disclosure are not particularly limited, so long as they provide light of suitable wavelength(s) and brightness for the light detection devices 854 to make an accurate reading of the colored light reflected from the detection membrane 812.

It should also be understood that the detection membrane 812 can include one or more stabilizing agents 832 as shown in FIGS. 8A-8F. Such stabilizing agents 832 can include neo silk protein saver; mannitol, trehalose, or other sugars; polypropylene glycol-polyethylene glycol block copolymers or other hydrophilic-hydrophobic block copolymers; or a combination thereof.

Figure 9:
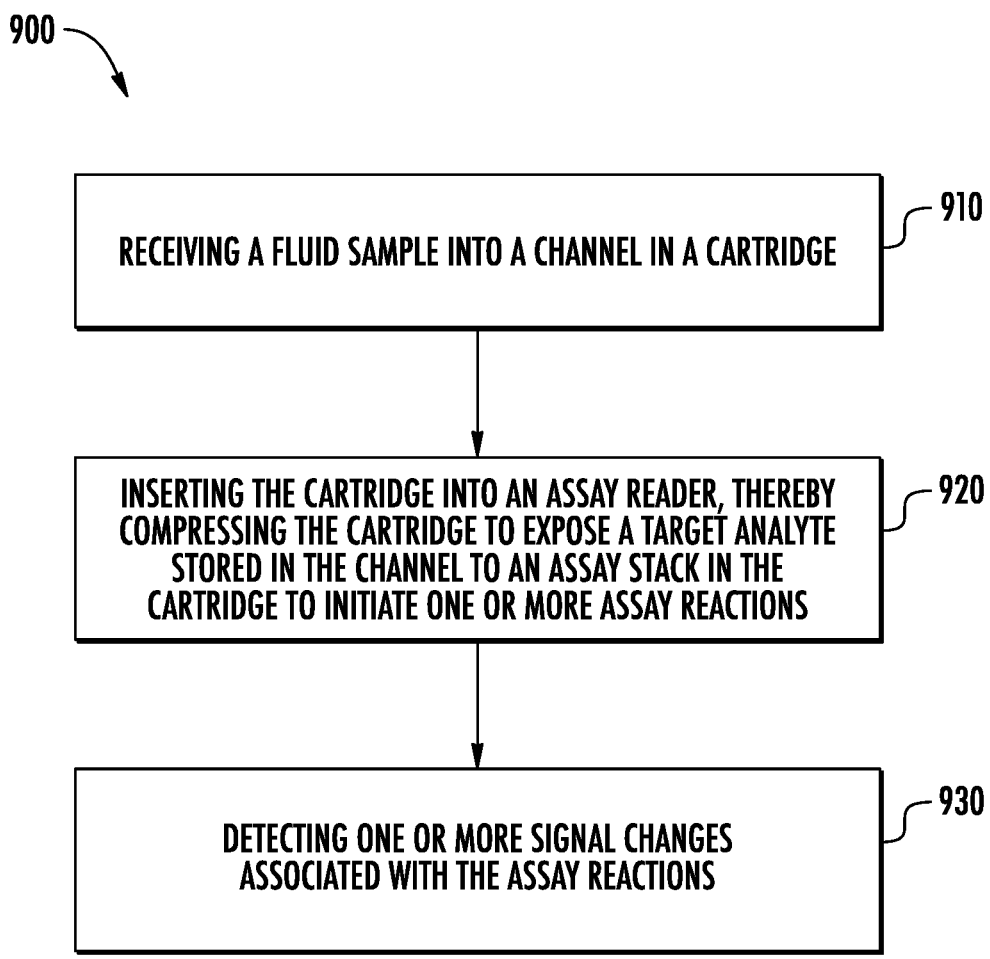
FIG. 9 shows a flow chart illustrating a method of using the assay system according to an exemplary implementation of the present disclosure.

FIG. 9 shows a flowchart that illustrates a method 900 of using of the assay system according to one embodiment of the present disclosure to perform a plurality of assays. The method 900 includes step 910, which involves receiving a fluid sample that may contain a target analyte or analyte of interest into a channel in a cartridge. Step 920 involves inserting the cartridge into an assay reader, thereby compressing the cartridge to expose a target analyte stored in the channel to an assay stack in the cartridge to initiate one or more assay reactions. Step 930 involves detecting one or more signal changes associated with the plurality of assay reactions. The method 900 can include any additional steps that would be understood by one of ordinary skill in the art to detect the one or more signal changes via the various components of the metering stack and assay stack described in detail above.

Figure 10:
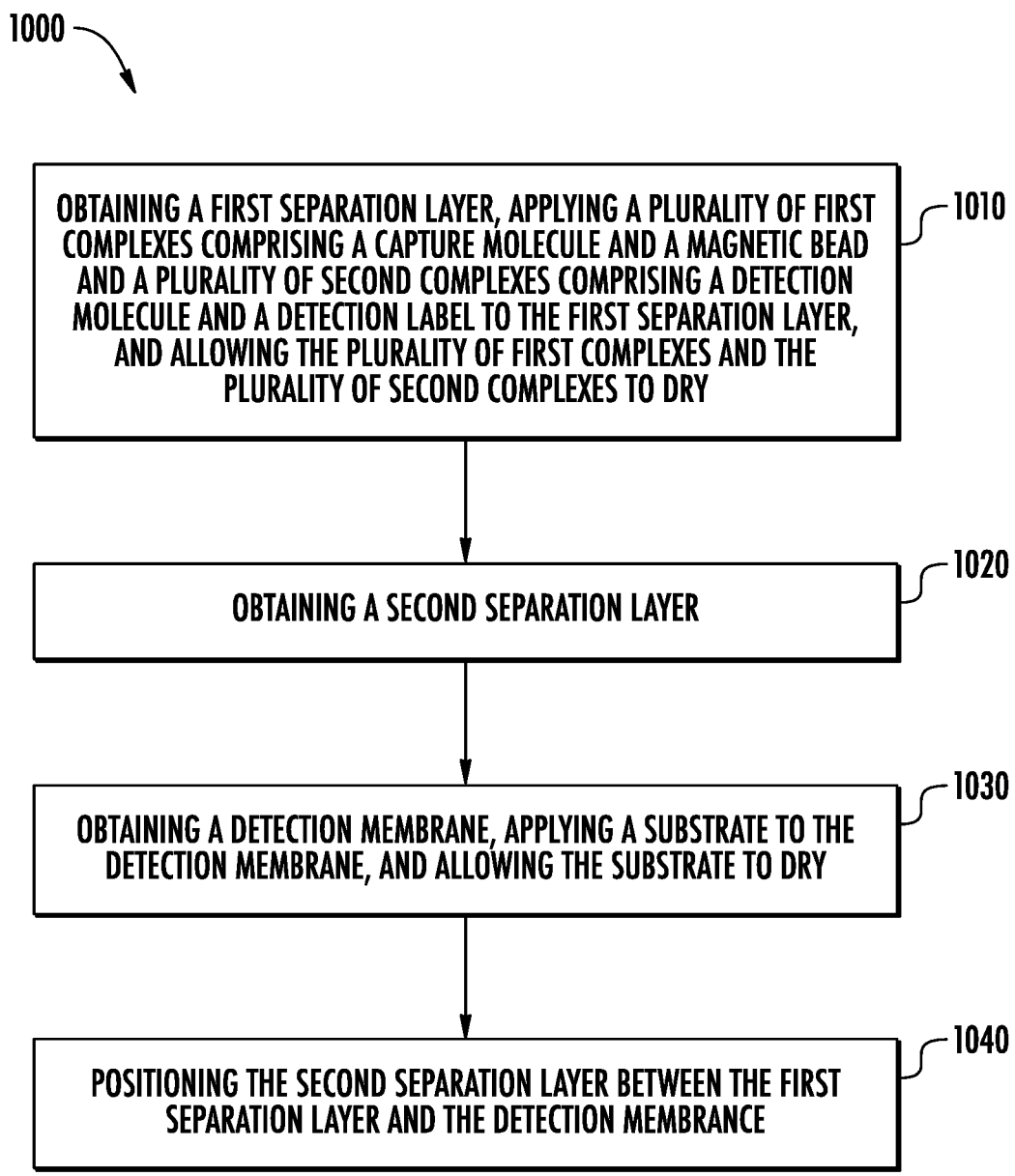
FIG. 10 shows a flow chart illustrating a method of manufacturing a cartridge according to one exemplary implementation of the present disclosure.

FIG. 10 shows a flowchart that illustrates a method 1000 of fabricating a cartridge according to one embodiment of the present disclosure. The method includes the steps of obtaining a first separation layer, applying a plurality of first complexes comprising a capture molecule and a magnetic bead and a plurality of second complexes comprising a detection molecule and a detection label to the plasma separation membrane, and allowing the plurality of first complexes and the plurality of second complexes to dry; (step 1010) and obtaining a second separation layer (step 1020). The method 1000 also includes the step of obtaining a detection membrane, applying a substrate to the detection membrane, and allowing the substrate to dry (step 1030). Further, the method 1000 also includes the step of positioning the second separation layer between the first separation layer and the detection membrane. In this method the substrate interacts with the detection label to elicit a quantifiable response in the presence of a target analyte in a fluid sample that is introduced to the cartridge. Further, the quantifiable response corresponds to an amount of detection molecule present in the detection membrane; and the amount of detection molecule present in the color detection membrane corresponds to an amount of the target analyte present in the fluid sample.

While various embodiments of the present disclosure have been described above, it should be understood that they have been presented by way of example only, and not by way of limitation. Likewise, the various diagrams may depict an example architectural or other configuration for the disclosure, which is done to aid in understanding the features and functionality that can be included in the disclosure. The disclosure is not restricted to the illustrated example architectures or configurations, but can be implemented using a variety of alternative architectures and configurations. Additionally, although the disclosure is described above in terms of various exemplary embodiments and implementations, it should be understood that the various features and functionality described in one or more of the individual embodiments are not limited in their applicability to the particular embodiment with which they are described. They instead can be applied, alone or in some combination, to one or more of the other embodiments of the disclosure, whether or not such embodiments are described, and whether or not such features are presented as being a part of a described embodiment. Thus, the breadth and scope of the present disclosure should not be limited by any of the above-described exemplary embodiments.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated. Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' 'preferred,' 'desired,' or 'desirable,' and words of similar meaning should not be understood as implying that certain features are critical, essential, or even important to the structure or function of the present disclosure, but instead as merely intended to highlight alternative or additional features that may or may not be utilized in a particular embodiment of the present disclosure. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

Where a range of values is provided, it is understood that the upper and lower limit, and each intervening value between the upper and lower limit of the range is encompassed within the embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

All of the features disclosed in this specification (including any accompanying exhibits, claims, abstract and drawings), and/or all of the steps of any method or process so disclosed, may be combined in any combination, except combinations where at least some of such features and/or steps are mutually exclusive. The disclosure is not restricted to the details of any foregoing embodiments. The disclosure extends to any novel one, or any novel combination, of the features disclosed in this specification (including any accompanying claims, abstract and drawings), or to any novel one, or any novel combination, of the steps of any method or process so disclosed.

While the present subject matter has been described in detail with respect to various specific example embodiments thereof, each example is provided by way of explanation, not limitation of the disclosure. Those skilled in the art, upon attaining an understanding of the foregoing, can readily produce alterations to, variations of, and equivalents to such embodiments. Accordingly, the subject disclosure does not preclude inclusion of such modifications, variations and/or additions to the present subject matter as would be readily apparent to one of ordinary skill in the art. For instance, features illustrated or described as part of one embodiment can be used with another embodiment to yield a still further embodiment. Thus, it is intended that the present disclosure cover such alterations, variations, and equivalents.

What is claimed is:

1. A cartridge for collecting a target analyte contained in a fluid sample and performing an assay on the target analyte, wherein the cartridge comprises:
   an assay stack, wherein the assay stack comprises:
      a first separation layer;
      a plurality of first complexes comprising a capture molecule and a magnetic bead;
      a plurality of second complexes comprising a detection molecule and a detection label;
      a second separation layer, wherein the second separation layer comprises a hydrophobic membrane, a low molecular weight cut-off membrane, or a combination thereof; and
      a detection membrane, wherein the detection membrane includes a substrate that interacts with the detection label to elicit a quantifiable response in the presence of the target analyte, wherein the quantifiable response corresponds to an amount of detection molecule present in the detection membrane, wherein the amount of detection molecule present in the detection membrane corresponds to an amount of the target analyte present in the fluid sample, wherein the second separation layer allows for a third complex comprising the target analyte bound to: (a) one of the first complexes and (b) one of the second complexes to pass to the detection membrane in the presence of an activated electromagnet.

2. The cartridge according to claim 1, wherein the second separation layer prevents passage of any unbound second complexes to the detection membrane.

3. The cartridge according to claim 1, wherein the second separation layer includes a hydrophilic treatment.

4. The cartridge according to claim 3, wherein the hydrophilic treatment is a coating that comprises a surfactant.

5. The cartridge according to claim 1, wherein the target analyte is contained within a fluid sample selected from the group consisting of blood, saliva, sweat, urine, lymph, tears, synovial fluid, breast milk, serum, plasma, bile, or a component thereof.

6. The cartridge according to claim 5, wherein the fluid sample is blood and the first separation layer is a plasma separation membrane that prevents erythrocytes from contacting the second separation layer.

7. The cartridge according to any claim 1, wherein the detection label comprises a peroxidase enzyme.

8. The cartridge according to claim 7, wherein the substrate comprises a reagent for the peroxidase enzyme.

9. The cartridge according to claim 1, wherein the cartridge is configured to perform an assay on the target analyte without any wash steps or moving parts.

10. The cartridge according to claim 1, wherein at least one component of the cartridge is compressible, thereby allowing for an uncompressed state and a compressed state of the cartridge.

11. The cartridge according to claim 10, further comprising a metering stack configured to receive and distribute the fluid sample containing the target analyte along a channel of the cartridge, wherein the channel has a bottom that comprises a porous or mesh material, further wherein the metering stack includes one or more venting holes in communication with the channel.

12. The cartridge according to claim 11, wherein a spacer material is disposed between the metering stack and the assay stack, wherein the spacer material provides a gap between the metering stack and the assay stack that prevents the target analyte from flowing from the metering stack into the assay stack when the cartridge is in the uncompressed state.

13. The cartridge according to claim 11, wherein the porous or mesh material permits the target analyte to flow from the metering stack to the assay stack upon compression of the at least one component of the cartridge.

* * * * *